(12) United States Patent
Zucherman et al.

(10) Patent No.: US 7,481,839 B2
(45) Date of Patent: Jan. 27, 2009

(54) BIORESORBABLE INTERSPINOUS PROCESS IMPLANT FOR USE WITH INTERVERTEBRAL DISK REMEDIATION OR REPLACEMENT IMPLANTS AND PROCEDURES

(75) Inventors: James F. Zucherman, San Francisco, CA (US); Ken Y. Hsu, San Francisco, CA (US)

(73) Assignee: Kyphon SARL, Neuchatel (CH)

( * ) Notice: Subject to any disclaimer, the term of this patent is extended or adjusted under 35 U.S.C. 154(b) by 568 days.

(21) Appl. No.: 10/995,626

(22) Filed: Nov. 23, 2004

(65) Prior Publication Data
US 2005/0196420 A1    Sep. 8, 2005

Related U.S. Application Data

(60) Provisional application No. 60/526,353, filed on Dec. 2, 2003, provisional application No. 60/526,215, filed on Dec. 2, 2003.

(51) Int. Cl.
A61F 2/44 (2006.01)

(52) U.S. Cl. .................. 623/17.11; 623/17.16

(58) Field of Classification Search ... 623/17.11–17.16; 606/60–62, 72
See application file for complete search history.

(56) References Cited

U.S. PATENT DOCUMENTS

| | | | |
|---|---|---|---|
| 2,456,806 A | 12/1948 | Wolffe | |
| 2,677,369 A | 5/1954 | Knowles | |
| 3,426,364 A | 2/1969 | Lumb | |
| 3,867,728 A | 2/1975 | Stubstad et al. | |
| 3,875,595 A | 4/1975 | Froning | |
| 4,309,777 A | 1/1982 | Patil | |
| 4,338,926 A | 7/1982 | Kummer et al. | |
| 4,349,921 A | 9/1982 | Kuntz | |
| 4,369,769 A | 1/1983 | Edwards | |
| 4,401,112 A * | 8/1983 | Rezaian | 606/279 |
| 4,479,491 A | 10/1984 | Martin | |
| 4,501,269 A | 2/1985 | Bagby | |
| 4,553,273 A | 11/1985 | Wu | |
| 4,554,914 A | 11/1985 | Kapp et al. | |
| 4,599,084 A | 7/1986 | Nashef | |
| 4,599,086 A | 7/1986 | Doty | |
| 4,636,217 A | 1/1987 | Ogilvie | |
| 4,657,550 A | 4/1987 | Daher | |

(Continued)

FOREIGN PATENT DOCUMENTS

CA    2015507    1/1991

(Continued)

OTHER PUBLICATIONS

Int'l Search Report for PCT/US04/4-134, Jul. 29, 2005.

(Continued)

Primary Examiner—Alvin J Stewart
(74) Attorney, Agent, or Firm—Coats and Bennett PLI

(57) ABSTRACT

A device for implantation between interspinous processes made of bioresorbable materials is described. The implant has a spacer that can be placed between adjacent spinous processes to limit the movement of the vertebrae. Once inserted between interspinous processes, the implant acts to limit extension (backward bending) of the spine without inhibiting the flexion (forward bending) of the spinal column. The device is used as an adjunct to repair or regeneration of an intervertebral disk.

56 Claims, 9 Drawing Sheets

U.S. PATENT DOCUMENTS

| | | | |
|---|---|---|---|
| 4,685,447 A | 8/1987 | Iversen et al. |
| 4,696,290 A | 9/1987 | Steffee |
| 4,714,469 A | 12/1987 | Kenna |
| 4,743,256 A | 5/1988 | Brantigan |
| 4,759,766 A | 7/1988 | Büttner-Janz et al. |
| 4,759,769 A | 7/1988 | Hedman et al. |
| 4,772,287 A | 9/1988 | Ray et al. |
| 4,790,303 A | 12/1988 | Steffee |
| 4,834,757 A | 5/1989 | Brantigan |
| 4,863,477 A | 9/1989 | Monson |
| 4,874,389 A | 10/1989 | Downey |
| 4,878,915 A | 11/1989 | Brantigan |
| 4,904,260 A | 2/1990 | Ray et al. |
| 4,904,261 A | 2/1990 | Dove et al. |
| 4,911,718 A | 3/1990 | Lee et al. |
| 4,932,969 A | 6/1990 | Frey et al. |
| 4,932,975 A | 6/1990 | Main et al. |
| 4,936,848 A | 6/1990 | Bagby |
| 4,946,378 A | 8/1990 | Hirayama et al. |
| 4,961,740 A | 10/1990 | Ray et al. |
| 4,969,888 A | 11/1990 | Scholten et al. |
| 4,997,432 A | 3/1991 | Keller |
| 5,002,576 A | 3/1991 | Fuhrmann et al. |
| 5,015,247 A | 5/1991 | Michelson |
| 5,026,373 A * | 6/1991 | Ray et al. ................. 606/86 A |
| 5,035,716 A | 7/1991 | Downey |
| 5,047,055 A | 9/1991 | Bao et al. |
| 5,055,104 A | 10/1991 | Ray |
| 5,059,193 A | 10/1991 | Kuslich |
| 5,059,194 A | 10/1991 | Michelson |
| 5,071,437 A | 12/1991 | Steffee |
| 5,092,866 A * | 3/1992 | Breard et al. ................. 606/54 |
| 5,108,438 A | 4/1992 | Stone |
| 5,108,442 A | 4/1992 | Smith |
| 5,122,130 A | 6/1992 | Keller |
| 5,123,926 A | 6/1992 | Pisharodi |
| 5,167,662 A | 12/1992 | Hayes et al. |
| 5,171,280 A | 12/1992 | Baumgartner |
| 5,171,281 A | 12/1992 | Parsons et al. |
| 5,180,381 A * | 1/1993 | Aust et al. ................. 606/280 |
| 5,192,326 A | 3/1993 | Bao et al. |
| 5,192,327 A | 3/1993 | Brantigan |
| 5,246,458 A | 9/1993 | Graham |
| 5,258,031 A | 11/1993 | Salib et al. |
| 5,258,043 A | 11/1993 | Stone |
| 5,263,953 A | 11/1993 | Bagby |
| 5,290,312 A | 3/1994 | Kojimoto et al. |
| 5,306,307 A | 4/1994 | Senter |
| 5,306,308 A | 4/1994 | Gross et al. |
| 5,306,309 A | 4/1994 | Wagner et al. |
| 5,313,962 A | 5/1994 | Obenchain |
| 5,314,477 A | 5/1994 | Marnay |
| 5,314,478 A | 5/1994 | Oka et al. |
| 5,320,644 A | 6/1994 | Baumgartner |
| 5,336,223 A | 8/1994 | Rogers |
| 5,350,397 A | 9/1994 | Palermo et al. |
| 5,354,302 A | 10/1994 | Ko |
| 5,360,430 A | 11/1994 | Lin |
| 5,366,508 A | 11/1994 | Brekke |
| 5,370,693 A | 12/1994 | Kelman et al. |
| 5,370,697 A | 12/1994 | Baumgartner |
| 5,375,823 A | 12/1994 | Navas |
| 5,383,884 A | 1/1995 | Summers |
| 5,390,683 A | 2/1995 | Pisharodi |
| 5,395,317 A | 3/1995 | Kambin |
| 5,395,372 A | 3/1995 | Holt et al. |
| 5,397,364 A | 3/1995 | Kozak et al. |
| 5,401,269 A | 3/1995 | Büttner-Janz et al. |
| 5,415,704 A | 5/1995 | Davidson |
| 5,423,816 A | 6/1995 | Lin |
| 5,423,817 A | 6/1995 | Lin |
| 5,425,772 A | 6/1995 | Brantigan |
| 5,425,773 A | 6/1995 | Boyd et al. |
| 5,425,777 A | 6/1995 | Sarkisian et al. |
| 5,431,658 A | 7/1995 | Moskovich |
| 5,439,464 A | 8/1995 | Shapiro |
| 5,443,514 A | 8/1995 | Steffee |
| 5,443,515 A | 8/1995 | Cohen et al. |
| 5,445,639 A | 8/1995 | Kuslich et al. |
| 5,456,722 A | 10/1995 | McLeod et al. |
| 5,458,638 A | 10/1995 | Kuslich et al. |
| 5,458,641 A * | 10/1995 | Ramirez Jimenez ..... 623/17.11 |
| 5,458,642 A | 10/1995 | Beer et al. |
| 5,458,643 A | 10/1995 | Oka et al. |
| 5,480,401 A | 1/1996 | Navas |
| 5,480,442 A | 1/1996 | Bertagnoli |
| 5,484,437 A | 1/1996 | Michelson |
| 5,489,307 A | 2/1996 | Kuslich et al. |
| 5,489,308 A | 2/1996 | Kuslich et al. |
| 5,496,318 A * | 3/1996 | Howland et al. .............. 606/61 |
| 5,505,732 A | 4/1996 | Michelson |
| 5,507,816 A | 4/1996 | Bullivant |
| 5,514,180 A | 5/1996 | Heggeness et al. |
| 5,522,899 A | 6/1996 | Michelson |
| 5,531,793 A | 7/1996 | Kelman et al. |
| 5,534,023 A | 7/1996 | Henley |
| 5,534,028 A | 7/1996 | Bao et al. |
| 5,534,029 A | 7/1996 | Shima |
| 5,534,030 A | 7/1996 | Navarro et al. |
| 5,534,031 A | 7/1996 | Matsuzaki et al. |
| 5,540,689 A | 7/1996 | Sanders et al. |
| 5,545,229 A | 8/1996 | Parsons et al. |
| 5,549,679 A | 8/1996 | Kuslich |
| 5,554,191 A | 9/1996 | Lahille et al. |
| 5,556,431 A | 9/1996 | Büttner-Janz |
| 5,562,736 A | 10/1996 | Ray et al. |
| 5,562,738 A | 10/1996 | Boyd et al. |
| 5,571,109 A | 11/1996 | Bertagnoli |
| 5,571,189 A | 11/1996 | Kuslich |
| 5,571,190 A | 11/1996 | Ulrich et al. |
| 5,571,192 A | 11/1996 | Schönhöffer |
| 5,591,235 A | 1/1997 | Kuslich |
| 5,593,409 A | 1/1997 | Michelson |
| 5,599,279 A | 2/1997 | Slotman et al. |
| 5,601,556 A | 2/1997 | Pisharodi |
| 5,603,713 A | 2/1997 | Aust et al. |
| 5,609,634 A | 3/1997 | Voydeville |
| 5,609,635 A | 3/1997 | Michelson |
| 5,609,636 A | 3/1997 | Kohrs et al. |
| 5,620,458 A | 4/1997 | Green et al. |
| 5,645,592 A | 7/1997 | Nicolais et al. |
| 5,645,596 A | 7/1997 | Kim et al. |
| 5,645,597 A | 7/1997 | Krapiva |
| 5,645,598 A | 7/1997 | Brosnahan, III |
| 5,645,599 A | 7/1997 | Samani |
| 5,653,761 A | 8/1997 | Pisharodi |
| 5,653,762 A | 8/1997 | Pisharodi |
| 5,658,335 A | 8/1997 | Allen |
| 5,658,336 A | 8/1997 | Pisharodi |
| 5,658,337 A | 8/1997 | Kohrs et al. |
| 5,669,909 A | 9/1997 | Zdeblick et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,676,702 A | 10/1997 | Ratron |
| 5,683,463 A | 11/1997 | Godefroy et al. |
| 5,683,464 A | 11/1997 | Wagner et al. |
| 5,683,465 A | 11/1997 | Shinn et al. |
| 5,693,100 A | 12/1997 | Pisharodi |
| 5,697,889 A | 12/1997 | Slotman et al. |
| 5,697,977 A | 12/1997 | Pisharodi |
| 5,700,292 A | 12/1997 | Margulies |
| 5,702,449 A | 12/1997 | McKay |

| | | | | | | |
|---|---|---|---|---|---|---|
| 5,702,450 | A | 12/1997 | Bisserie | 6,096,038 | A | 8/2000 | Michelson |
| 5,702,454 | A | 12/1997 | Baumgartner | 6,096,080 | A | 8/2000 | Nicholson et al. |
| 5,702,455 | A | 12/1997 | Saggar | 6,099,531 | A | 8/2000 | Bonutti |
| 5,716,415 | A | 2/1998 | Steffee | 6,102,950 | A | 8/2000 | Vaccaro |
| 5,716,416 | A | 2/1998 | Lin | 6,110,210 | A | 8/2000 | Norton et al. |
| 5,741,253 | A | 4/1998 | Michelson | 6,111,164 | A | 8/2000 | Rainey et al. |
| 5,755,732 | A | 5/1998 | Green et al. | 6,113,637 | A | 9/2000 | Gill et al. |
| 5,755,796 | A | 5/1998 | Ibo et al. | 6,113,638 | A | 9/2000 | Williams et al. |
| 5,755,798 | A | 5/1998 | Papavero et al. | 6,113,639 | A | 9/2000 | Ray et al. |
| 5,766,252 | A | 6/1998 | Henry et al. | 6,120,502 | A | 9/2000 | Michelson |
| 5,772,661 | A | 6/1998 | Michelson | 6,120,503 | A | 9/2000 | Michelson |
| 5,776,196 | A | 7/1998 | Matsuzaki et al. | 6,123,705 | A | 9/2000 | Michelson |
| 5,776,199 | A | 7/1998 | Michelson | 6,126,689 | A | 10/2000 | Brett |
| 5,782,830 | A | 7/1998 | Farris | 6,127,597 | A | 10/2000 | Beyar et al. |
| 5,782,832 | A | 7/1998 | Larsen et al. | 6,129,763 | A | 10/2000 | Chauvin et al. |
| 5,782,919 | A | 7/1998 | Zdeblick et al. | 6,132,430 | A | 10/2000 | Wagner |
| 5,797,909 | A | 8/1998 | Michelson | 6,132,465 | A | 10/2000 | Ray et al. |
| 5,800,438 | A | 9/1998 | Tuke et al. | 6,136,001 | A | 10/2000 | Michelson |
| 5,800,550 | A | 9/1998 | Sertich | 6,136,031 | A | 10/2000 | Middleton |
| 5,824,093 | A | 10/1998 | Ray et al. | 6,139,579 | A | 10/2000 | Steffee et al. |
| 5,824,094 | A | 10/1998 | Serhan et al. | 6,146,420 | A * | 11/2000 | McKay ............. 623/17.16 |
| 5,827,328 | A | 10/1998 | Buttermann | 6,146,421 | A | 11/2000 | Gordon et al. |
| 5,836,948 | A | 11/1998 | Zucherman et al. | 6,146,422 | A | 11/2000 | Lawson |
| 5,860,973 | A | 1/1999 | Michelson | 6,149,650 | A | 11/2000 | Michelson |
| 5,860,977 | A * | 1/1999 | Zucherman et al. ........... 606/61 | 6,149,652 | A | 11/2000 | Zucherman et al. |
| 5,865,845 | A | 2/1999 | Thalgott | 6,149,686 | A | 11/2000 | Kuslich et al. |
| 5,865,846 | A | 2/1999 | Bryan et al. | 6,152,926 | A | 11/2000 | Zucherman et al. |
| 5,876,404 | A | 3/1999 | Zucherman et al. | 6,156,038 | A * | 12/2000 | Zucherman et al. ......... 606/249 |
| 5,885,292 | A | 3/1999 | Moskovitz et al. | 6,156,067 | A | 12/2000 | Bryan et al. |
| 5,885,299 | A | 3/1999 | Winslow et al. | 6,159,215 | A | 12/2000 | Urbahns et al. |
| 5,888,222 | A | 3/1999 | Coates et al. | 6,162,252 | A | 12/2000 | Kuras et al. |
| 5,888,224 | A | 3/1999 | Beckers et al. | 6,165,218 | A | 12/2000 | Husson et al. |
| 5,888,226 | A | 3/1999 | Rogozinski | 6,176,882 | B1 | 1/2001 | Biedermann et al. |
| 5,888,227 | A | 3/1999 | Cottle | 6,179,874 | B1 | 1/2001 | Cauthen |
| 5,891,147 | A | 4/1999 | Moskovitz et al. | 6,183,471 | B1 * | 2/2001 | Zucherman et al. ......... 606/249 |
| 5,893,889 | A | 4/1999 | Harrington | 6,190,387 | B1 | 2/2001 | Zucherman et al. |
| 5,893,890 | A | 4/1999 | Pisharodi | 6,190,414 | B1 | 2/2001 | Young et al. |
| 5,895,426 | A | 4/1999 | Scarborough et al. | 6,193,757 | B1 | 2/2001 | Foley et al. |
| 5,895,427 | A | 4/1999 | Kuslich et al. | 6,206,922 | B1 | 3/2001 | Zdeblick et al. |
| 5,895,428 | A | 4/1999 | Berry | 6,210,412 | B1 | 4/2001 | Michelson |
| 5,899,941 | A | 5/1999 | Nishijima et al. | 6,224,595 | B1 | 5/2001 | Michelson |
| 5,906,616 | A | 5/1999 | Pavlov et al. | 6,224,607 | B1 | 5/2001 | Michelson |
| 5,919,235 | A | 7/1999 | Husson et al. | 6,224,630 | B1 * | 5/2001 | Bao et al. ................ 623/17.16 |
| 5,928,284 | A | 7/1999 | Mehdizadeh | 6,224,631 | B1 | 5/2001 | Kohrs |
| 5,944,754 | A | 8/1999 | Vacanti | 6,228,118 | B1 | 5/2001 | Gordon |
| 5,945,115 | A | 8/1999 | Dunn et al. | 6,231,609 | B1 | 5/2001 | Mehdizadeh |
| 5,961,554 | A | 10/1999 | Jason et al. | 6,234,705 | B1 | 5/2001 | Troxell |
| 5,964,807 | A | 10/1999 | Gan et al. | 6,235,030 | B1 | 5/2001 | Zucherman et al. |
| 5,976,186 | A | 11/1999 | Bao et al. | 6,238,397 | B1 | 5/2001 | Zucherman et al. |
| 5,980,572 | A | 11/1999 | Kim et al. | 6,241,769 | B1 | 6/2001 | Nicholson et al. |
| 5,984,967 | A | 11/1999 | Zdeblick et al. | 6,241,770 | B1 | 6/2001 | Michelson |
| 5,989,291 | A | 11/1999 | Ralph et al. | 6,241,771 | B1 | 6/2001 | Gresser et al. |
| 6,001,130 | A | 12/1999 | Bryan et al. | 6,245,072 | B1 | 6/2001 | Zdeblick et al. |
| 6,004,573 | A | 12/1999 | Rathi et al. | 6,245,108 | B1 | 6/2001 | Biscup |
| 6,005,162 | A | 12/1999 | Constantz | 6,258,125 | B1 | 7/2001 | Paul et al. |
| 6,019,792 | A | 2/2000 | Cauthen | 6,261,296 | B1 | 7/2001 | Aebi et al. |
| 6,019,793 | A | 2/2000 | Perren et al. | 6,264,655 | B1 | 7/2001 | Pisharodi |
| 6,022,376 | A | 2/2000 | Assell et al. | 6,264,656 | B1 | 7/2001 | Michelson |
| 6,039,761 | A | 3/2000 | Li et al. | 6,264,695 | B1 * | 7/2001 | Stoy ....................... 623/17.16 |
| 6,039,763 | A | 3/2000 | Shelokov | 6,270,498 | B1 | 8/2001 | Michelson |
| 6,042,582 | A | 3/2000 | Ray | 6,277,149 | B1 | 8/2001 | Boyle et al. |
| 6,045,579 | A | 4/2000 | Hochshuler et al. | 6,280,444 | B1 | 8/2001 | Zucherman et al. |
| 6,045,580 | A | 4/2000 | Scarborough et al. | 6,280,475 | B1 | 8/2001 | Bao et al. |
| 6,048,342 | A | 4/2000 | Zucherman et al. | 6,287,343 | B1 | 9/2001 | Kuslich et al. |
| 6,051,648 | A | 4/2000 | Rhee et al. | 6,290,724 | B1 | 9/2001 | Marino |
| 6,068,630 | A * | 5/2000 | Zucherman et al. ......... 606/249 | 6,296,645 | B1 | 10/2001 | Hover et al. |
| 6,074,390 | A | 6/2000 | Zucherman et al. | 6,296,664 | B1 | 10/2001 | Middleton |
| 6,080,155 | A | 6/2000 | Michelson | 6,296,665 | B1 | 10/2001 | Strnad et al. |
| 6,080,158 | A | 6/2000 | Lin | 6,302,914 | B1 | 10/2001 | Michelson |
| 6,080,193 | A | 6/2000 | Hochshuler et al. | 6,309,421 | B1 | 10/2001 | Pisharodi |
| 6,086,613 | A | 7/2000 | Camino et al. | 6,311,562 | B1 | 11/2001 | Hanada |
| 6,090,112 | A | 7/2000 | Zucherman et al. | 6,315,795 | B1 | 11/2001 | Scarborough et al. |
| 6,093,205 | A * | 7/2000 | McLeod et al. ........... 623/17.16 | 6,315,797 | B1 | 11/2001 | Middleton |

| | | | | | | |
|---|---|---|---|---|---|---|
| 6,325,827 | B1 | 12/2001 | Lin | 6,530,955 | B2 | 3/2003 | Boyle et al. |
| 6,332,882 | B1 | 12/2001 | Zucherman et al. | 6,540,785 | B2 | 4/2003 | Gill et al. |
| 6,332,883 | B1 | 12/2001 | Zucherman et al. | 6,547,823 | B2 | 4/2003 | Scarborough et al. |
| 6,332,894 | B1 | 12/2001 | Stalcup et al. | 6,548,002 | B2 | 4/2003 | Gresser et al. |
| 6,342,074 | B1 | 1/2002 | Simpson | 6,554,863 | B2 | 4/2003 | Paul et al. |
| 6,348,071 | B1 | 2/2002 | Steffee et al. | 6,558,386 | B1 | 5/2003 | Cragg |
| 6,350,283 | B1 | 2/2002 | Michelson | 6,558,387 | B2 | 5/2003 | Errico et al. |
| 6,364,880 | B1 | 4/2002 | Michelson | 6,558,390 | B2 | 5/2003 | Cragg |
| 6,368,350 | B1 | 4/2002 | Erickson et al. | 6,558,423 | B1 | 5/2003 | Michelson |
| 6,368,351 | B1 | 4/2002 | Glenn et al. | 6,558,424 | B2 | 5/2003 | Thalgott |
| 6,371,984 | B1 | 4/2002 | Van Dyke et al. | 6,562,073 | B2 | 5/2003 | Foley |
| 6,371,988 | B1 | 4/2002 | Pafford et al. | 6,562,074 | B2 | 5/2003 | Gerbec et al. |
| 6,371,989 | B1 | 4/2002 | Chauvin et al. | 6,565,570 | B2 | 5/2003 | Sterett et al. |
| 6,379,355 | B1 | 4/2002 | Zucherman et al. | 6,569,201 | B2 | 5/2003 | Moumene et al. |
| 6,379,385 | B1 | 4/2002 | Kalas et al. | 6,572,653 | B1 | 6/2003 | Simonson |
| 6,383,221 | B1 | 5/2002 | Scarborough et al. | 6,572,654 | B1 | 6/2003 | Santilli |
| 6,391,030 | B1 | 5/2002 | Wagner et al. | 6,575,982 | B1 | 6/2003 | Bonutti |
| 6,391,058 | B1 | 5/2002 | Kuslich et al. | 6,576,016 | B1 | 6/2003 | Hochshuler et al. |
| 6,395,030 | B1 | 5/2002 | Songer et al. | 6,576,017 | B2 | 6/2003 | Foley et al. |
| 6,395,031 | B1 | 5/2002 | Foley et al. | 6,579,318 | B2 | 6/2003 | Varga et al. |
| 6,395,032 | B1 | 5/2002 | Gauchet | 6,579,320 | B1 | 6/2003 | Gauchet et al. |
| 6,395,034 | B1 | 5/2002 | Suddaby | 6,579,321 | B1 | 6/2003 | Gordon et al. |
| 6,402,785 | B1 | 6/2002 | Zdeblick et al. | 6,582,431 | B1* | 6/2003 | Ray ............................ 606/61 |
| 6,409,766 | B1 | 6/2002 | Brett | 6,582,432 | B1 | 6/2003 | Michelson |
| 6,413,278 | B1 | 7/2002 | Marchosky | 6,582,437 | B2 | 6/2003 | Dorchak et al. |
| 6,416,551 | B1 | 7/2002 | Keller | 6,582,468 | B1 | 6/2003 | Gauchet |
| 6,419,676 | B1 | 7/2002 | Zucherman et al. | 6,610,089 | B1 | 8/2003 | Liu et al. |
| 6,419,677 | B2 | 7/2002 | Zucherman et al. | 6,623,492 | B1* | 9/2003 | Berube et al. ................ 606/151 |
| 6,419,704 | B1 | 7/2002 | Ferree | 6,626,944 | B1* | 9/2003 | Taylor ..................... 623/17.16 |
| 6,419,706 | B1 | 7/2002 | Graf | 6,682,562 | B2 | 1/2004 | Viart et al. |
| 6,423,063 | B1 | 7/2002 | Bonutti | 6,699,246 | B2 | 3/2004 | Zucherman et al. |
| 6,423,095 | B1 | 7/2002 | Van Hoeck et al. | 6,706,068 | B2 | 3/2004 | Ferree |
| 6,425,920 | B1 | 7/2002 | Hamada | 6,706,070 | B1 | 3/2004 | Wagner et al. |
| 6,432,106 | B1 | 8/2002 | Fraser | 6,733,534 | B2* | 5/2004 | Sherman ................... 623/17.16 |
| 6,436,098 | B1 | 8/2002 | Michelson | 6,740,118 | B2 | 5/2004 | Eisermann et al. |
| 6,436,119 | B1 | 8/2002 | Erb et al. | 6,743,257 | B2* | 6/2004 | Castro ..................... 623/17.16 |
| 6,436,140 | B1 | 8/2002 | Liu et al. | 6,755,841 | B2 | 6/2004 | Fraser et al. |
| 6,436,142 | B1 | 8/2002 | Paes et al. | 6,770,095 | B2 | 8/2004 | Grinberg et al. |
| 6,440,168 | B1 | 8/2002 | Cauthen | 6,786,908 | B2 | 9/2004 | Hover et al. |
| 6,440,169 | B1 | 8/2002 | Elberg et al. | 6,893,466 | B2 | 5/2005 | Trieu |
| 6,443,990 | B1 | 9/2002 | Aebi et al. | 6,902,566 | B2* | 6/2005 | Zucherman et al. ........... 606/61 |
| 6,447,512 | B1 | 9/2002 | Landry et al. | 7,074,239 | B1* | 7/2006 | Cornwall et al. ......... 623/17.11 |
| 6,447,544 | B1 | 9/2002 | Michelson | 7,128,760 | B2* | 10/2006 | Michelson ............... 623/17.15 |
| 6,447,547 | B1 | 9/2002 | Michelson | 7,156,877 | B2* | 1/2007 | Lotz et al. ............... 623/17.16 |
| 6,451,019 | B1 | 9/2002 | Zucherman et al. | 7,238,204 | B2* | 7/2007 | Le Couedic et al. ...... 623/17.11 |
| 6,451,020 | B1 | 9/2002 | Zucherman et al. | 7,306,628 | B2* | 12/2007 | Zucherman et al. ...... 623/17.11 |
| 6,454,804 | B1 | 9/2002 | Ferree | 7,335,203 | B2* | 2/2008 | Winslow et al. .............. 606/61 |
| 6,454,807 | B1 | 9/2002 | Jackson | 2002/0123750 | A1* | 9/2002 | Eisermann et al. ........... 606/69 |
| 6,458,131 | B1 | 10/2002 | Ray | 2002/0128715 | A1 | 9/2002 | Bryan et al. |
| 6,458,159 | B1 | 10/2002 | Thalgott | 2002/0156531 | A1* | 10/2002 | Felt et al. ................. 623/17.16 |
| 6,461,359 | B1 | 10/2002 | Tribus et al. | 2003/0208273 | A1 | 11/2003 | Eisermann et al. |
| 6,468,310 | B1 | 10/2002 | Ralph et al. | 2004/0073313 | A1 | 4/2004 | Link et al. |
| 6,471,724 | B2 | 10/2002 | Zdeblick et al. | 2004/0106998 | A1 | 6/2004 | Ferree |
| 6,475,219 | B1 | 11/2002 | Shelokov | 2004/0117022 | A1 | 6/2004 | Marnay et al. |
| 6,478,796 | B2 | 11/2002 | Zucherman et al. | 2004/0138750 | A1 | 7/2004 | Mitchell |
| 6,478,822 | B1 | 11/2002 | Leroux et al. | 2004/0143332 | A1 | 7/2004 | Krueger |
| 6,478,823 | B1 | 11/2002 | Michelson | 2004/0225360 | A1 | 11/2004 | Malone |
| 6,482,233 | B1 | 11/2002 | Aebi et al. | 2004/0225365 | A1 | 11/2004 | Eisermann et al. |
| 6,482,235 | B1 | 11/2002 | Lambrecht et al. | 2004/0225366 | A1 | 11/2004 | Eisermann et al. |
| 6,485,517 | B1 | 11/2002 | Michelson | 2005/0085812 | A1 | 4/2005 | Sherman et al. |
| 6,488,710 | B2 | 12/2002 | Besselink | | | | |
| 6,500,178 | B2 | 12/2002 | Zucherman et al. | | | | |
| 6,500,205 | B1 | 12/2002 | Michelson | | | | |
| 6,503,279 | B1 | 1/2003 | Webb et al. | | | | |
| 6,514,256 | B2 | 2/2003 | Zucherman et al. | | | | |
| 6,517,580 | B1 | 2/2003 | Ramadan et al. | | | | |
| 6,520,993 | B2 | 2/2003 | James et al. | | | | |
| 6,520,996 | B1 | 2/2003 | Manasas et al. | | | | |
| 6,524,312 | B2 | 2/2003 | Landry et al. | | | | |
| 6,527,773 | B1 | 3/2003 | Lin et al. | | | | |
| 6,527,804 | B2 | 3/2003 | Gauchet et al. | | | | |
| 6,527,806 | B2 | 3/2003 | Ralph et al. | | | | |
| 6,530,933 | B1 | 3/2003 | Yeung et al. | | | | |

FOREIGN PATENT DOCUMENTS

| | | |
|---|---|---|
| DE | 4012622 | 7/1991 |
| EP | 0307241 B1 | 3/1989 |
| FR | 2707864 | 1/1995 |
| FR | 2717066 | 9/1995 |
| FR | 2717068 | 9/1995 |
| FR | 2730156 A1 | 8/1996 |
| FR | 2780269 A1 | 12/1999 |
| FR | 2806614 A1 | 9/2001 |
| WO | WO 90/00037 | 1/1990 |
| WO | WO 95/31158 A | 11/1995 |

| | | |
|---|---|---|
| WO | WO 99/26562 | 6/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 00/23015 A1 | 4/2000 |
| WO | WO 01/01893 A1 | 1/2001 |
| WO | WO 01/89428 A2 | 11/2001 |

OTHER PUBLICATIONS

Ceramic Interspinous Block (CISB) Assisted Anterior Interbody Fusion, Haruo Tsuji, Norikazu Hirano, Yoshiharu Katoh, Hitoshi Ohshima, Hirokazu Ishihara, Hisao Matsui, and Yohihiko Hayashi, *Journal of Spinal Disorders* vol. 3. No. 1, pp. 77-86, c1990 Raven Press, Ltd., New York.

Instrumentation and Implants for Spinal Surgery, J. Dabb, *Diary of the XVIIIth Scientific Meeting of the PTO Tr/Pamietnik XVIII Zjazdu Naukowego PTO Tr/PZ,WL, Warszawa*, Link America Inc., 1971, 665.

Spinal Stenosis and Neurogenic Claudication, Richard W. Porter, MD, FRCS, FRCSE, *SPINE* vol. 21, No. 17, pp. 2046-2052, c1996, Lippincott-Raven Publishers.

Preliminary Design and Experimental Studies of a Novel Soft Implant for Correcting Sagittal Plan Instability in the Lumbar Spine, R.J.Minns, BEng, Msc, PhD, DscTech, and W.K.Walsh, FRCS, *SPINE* vol. 22, No. 16, pp. 1819-1827, c1997, Lippincott-Raven Publishers.

International Search Report for PCT/US06/10521 (mailed Nov. 22, 2006).

* cited by examiner

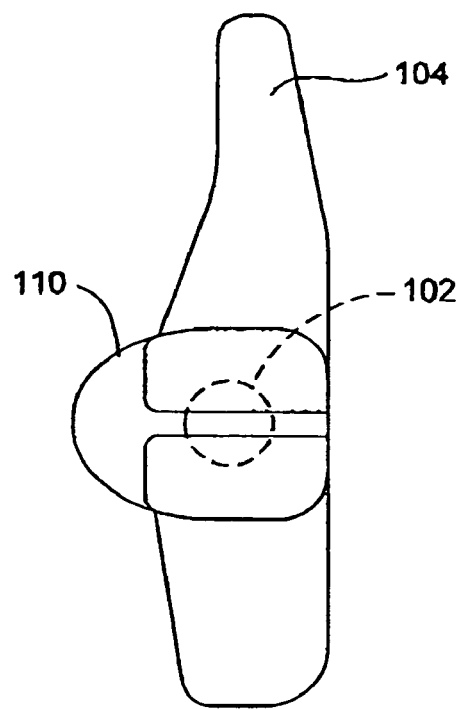
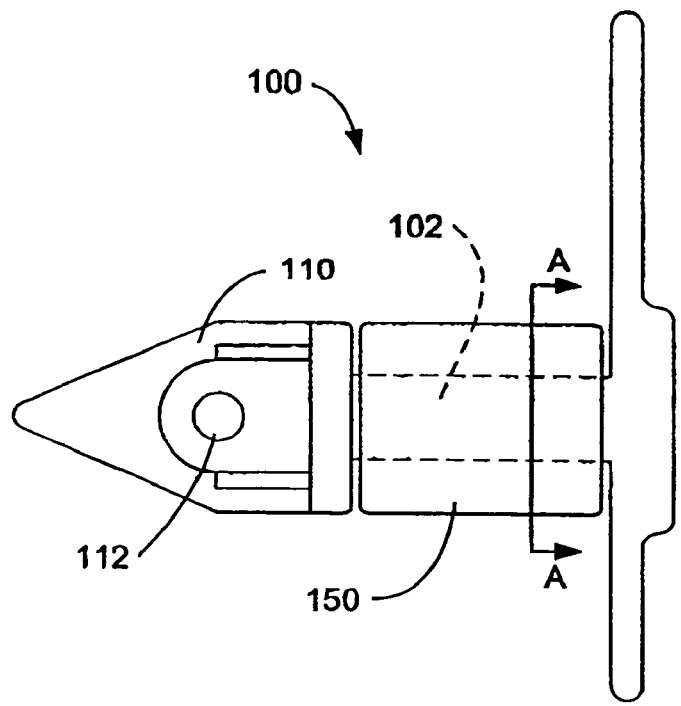
FIG. - 1B
FIG. - 1C
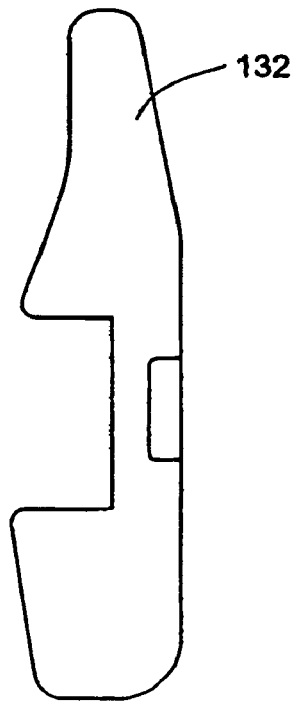
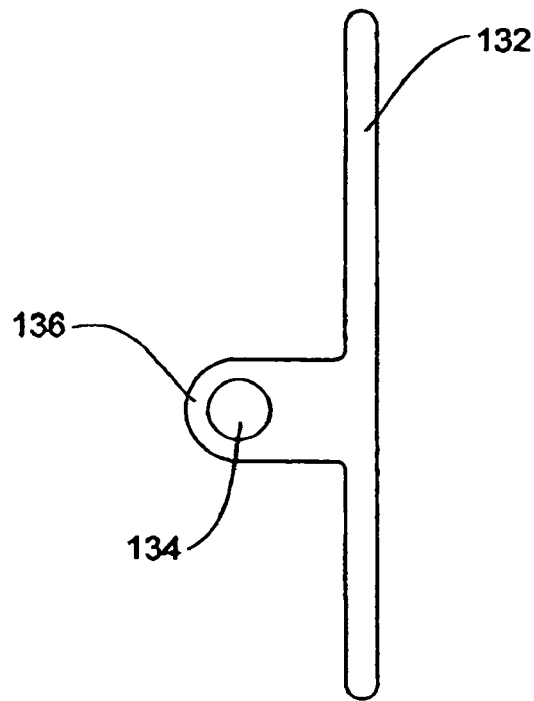
FIG. - 1D
FIG. - 1E (800)

Accessing intervertebral space (810)

↓

Restoring damaged disk (820)

↓

One of implanting bioresorbable device and distracting adjacent spinous processes (830)

↓

The other of implanting bioresorbable device and distracting adjacent spinous processes (840)

↓

Tethering the spinous processes (850), or, tethering the spinous processes and bioresorbable device if said device has at least one of a first wing, and a first wing and a second wing (855)

↓

Fastening the ends of the tether (860)

Fig. 8

BIORESORBABLE INTERSPINOUS PROCESS IMPLANT FOR USE WITH INTERVERTEBRAL DISK REMEDIATION OR REPLACEMENT IMPLANTS AND PROCEDURES

CLAIM OF PRIORITY

U.S. Provisional Patent Application No. 60/526,353 entitled BIORESORBABLE INTERSPINOUS PROCESS IMPLANT FOR USE WITH INTERVERTEBRAL DISK REMEDIATION OR REPLACEMENT IMPLANTS AND PROCEDURES, by James F. Zucherman et al., filed Dec. 2, 2003; U.S. Provisional Patent Application No. 60/526,215 entitled METHOD FOR REMEDIATION OF INTERVERTEBRAL DISKS, by James F. Zucherman et al., filed Dec. 2, 2003 both of which are incorporated herein by reference.

CROSS-REFERENCE TO RELATED APPLICATIONS

This application is related to U.S. patent application Ser. No. 10/230,505, filed Aug. 29, 2002, entitled "DEFLECTABLE SPACER FOR USE AS AN INTERSPINOUS PROCESS IMPLANT AND METHOD," U.S. Provisional Application No. 60/421,921, filed Oct. 29, 2002, entitled "INTERSPINOUS PROCESS APPARATUS AND METHOD WITH A SELECTABLY EXPANDABLE SPACER," and U.S. patent application Ser. No. 10/684,847, filed Oct. 14, 2003, entitled "INTERSPINOUS PROCESS APPARATUS AND METHOD FOR SELECTABLY EXPANDABLE SPACER," which are incorporated herein by reference. This application also is related to U.S. patent application Ser. No. 10/996,996, filed Nov. 23, 2004, entitled "METHOD FOR REMEDIATION OF INTERVERTEBRAL DISKS," which is incorporated herein by reference. This application is also related to U.S. patent application Ser. No. 10/037,236, filed Nov. 9, 2001, entitled "INTERSPINOUS PROCESS IMPLANT AND METHOD WITH DEFORMABLE SPACER," which is related to U.S. patent application Ser. No. 09/799,215, filed Mar. 5, 2001, entitled "SPINE DISTRACTION IMPLANT," which is related to U.S. patent application Ser. No. 09/473,173, filed Dec. 28, 1999, entitled "SPINE DISTRACTION IMPLANT," now U.S. Pat. No. 6,235,030, which is related to U.S. patent application Ser. No. 09/179,570, filed Oct. 27, 1998, entitled "SPINE DISTRACTION IMPLANT," now U.S. Pat. No. 6,048,342, which is related to U.S. patent application Ser. No. 09/474,037, filed Dec. 28, 1999, entitled "SPINE DISTRACTION IMPLANT," now U.S. Pat. No. 6,190,387, which is related to U.S. patent application Ser. No. 09/175,645, filed Oct. 20, 1998, entitled "SPINE DISTRACTION IMPLANT," now U.S. Pat. No. 6,068,630, and U.S. application Ser. No. 10/694,103, filed Oct. 27, 2003, entitled "INTERSPINOUS PROCESS IMPLANT WITH RADIOLUCENT SPACER AND LEAD-IN TISSUE EXPANDER." All of the above are incorporated herein by reference. This application is also related to U.S. patent application Ser. No. 10/684,669, filed Oct. 14, 2003, entitled "ARTIFICIAL VERTEBRAL DISK REPLACEMENT IMPLANT WITH TRANSLATING PIVOT POINT AND METHOD," U.S. Provisional Patent Application 60/526,724, filed Dec. 2, 2003, entitled "ARTIFICIAL VERTEBRAL DISK REPLACEMENT IMPLANT WITH TRANSLATING PIVOT POINT AND LATERAL IMPLANT METHOD," U.S. patent application Ser. No. 10/684,668, filed Oct. 14, 2003, entitled "ARTIFICIAL VERTEBRAL DISK REPLACEMENT IMPLANT WITH CROSSBAR SPACER AND METHOD," U.S. Provisional Application No. 60/517,973, filed Nov. 6, 2003, entitled "ARTIFICIAL VERTEBRAL DISK REPLACEMENT IMPLANT WITH CROSSBAR SPACER AND LATERAL IMPLANT METHOD," U.S. patent application Ser. No. 10/685,011, filed Oct. 14, 2003, entitled "ARTIFICIAL VERTEBRAL DISK REPLACEMENT IMPLANT WITH A SPACER AND METHOD," and U.S. Provisional Application No. 60/524,350, filed Nov. 21, 2003, entitled "ARTIFICIAL VERTEBRAL DISK REPLACEMENT IMPLANT WITH A SPACER AND LATERAL IMPLANT METHOD," all of which are also incorporated herein by reference.

BACKGROUND

This field of art of this disclosure is an interspinous process implant.

The spinal column is a biomechanical structure composed primarily of ligaments, muscles, vertebrae and intervertebral disks. The biomechanical functions of the spine include: (1) support of the body, which involves the transfer of the weight and the bending movements of the head, trunk and arms to the pelvis and legs, (2) complex physiological motion between these parts, and (3) protection of the spinal cord and the nerve roots.

As the present society ages, it is anticipated that there will be an increase in adverse spinal conditions which are characteristic of older people. By way of example, with aging comes an increase in spinal stenosis (including, but not limited to, central canal and lateral stenosis), and facet anthropathy. Spinal stenosis typically results from the thickening of the bones that make up the spinal column and is characterized by a reduction in the available space for the passage of blood vessels and nerves. Pain associated with such stenosis can be relieved by medication and/or surgery.

In addition, to spinal stenosis, and facet anthropathy, the incidence of damage to the intervertebral disks due to injury or degeneration is also common. The primary purpose of the intervertebral disk is as a shock absorber. The disk is constructed of an inner gel-like structure, the nucleus pulposus (the nucleus), and an outer rigid structure comprised of collagen fibers, the annulus fibrosus (the annulus). At birth, the disk is 80% water, and then gradually diminishes, becoming stiff. With age, disks may degenerate, and bulge, thin, herniate, or ossify. Additionally, damage to disks may occur as a result spinal cord trauma or injury.

Given an increasing need, there is increasing attention currently focused on devices and methods for remediation of conditions of the spine. Remediation includes replacement or repair, or both of an affected part or parts of the spine, as will be discussed in more detail subsequently. Regarding the evolution of remediation of damage to intervertebral disks, rigid fixation procedures resulting in fusion are still the most commonly performed, though trends suggest a move away from such procedures. Currently, areas evolving to address the shortcomings of fusion for remediation of disk damage include technologies and procedures that preserve or repair the annulus, that replace or repair the nucleus, and that utilize technology advancement on devices for total disk replacement. The trend away from fusion is driven by both issues concerning the quality of life for those suffering from damaged intervertebral disks, as well as responsible health care management. These issues drive the desire for procedures that are minimally invasive, can be tolerated by patients of all ages, especially seniors, and can be performed preferably on an out patient basis.

Accordingly, there is a need in the art for innovation in technologies and methods that advance the art in the area of minimally invasive intervertebral disk remediation, thereby enhancing the quality of life for those suffering from the condition, as well as responding to the current needs of health care management.

BRIEF DESCRIPTION OF THE DRAWINGS

FIGS. 1A-1F. FIG. 1A is a front plan view of an embodiment of an assembled the disclosed device; FIG. 1B is a left side view of what is shown in FIG. 1A, and FIG. 1C is a front plan view of FIG. 1A including a distraction guide, spacer, a central body and a first wing; FIG. 1D is a left side view of the second wing of FIG. 1A; FIG. 1E is a front plan view of the second wing of FIG. 1A; FIG. 1F is an end view of the spacer of FIG. 1A.

FIG. 8 depicts an embodiment of the method of the present invention.

DETAILED DESCRIPTION

Figure 1A:
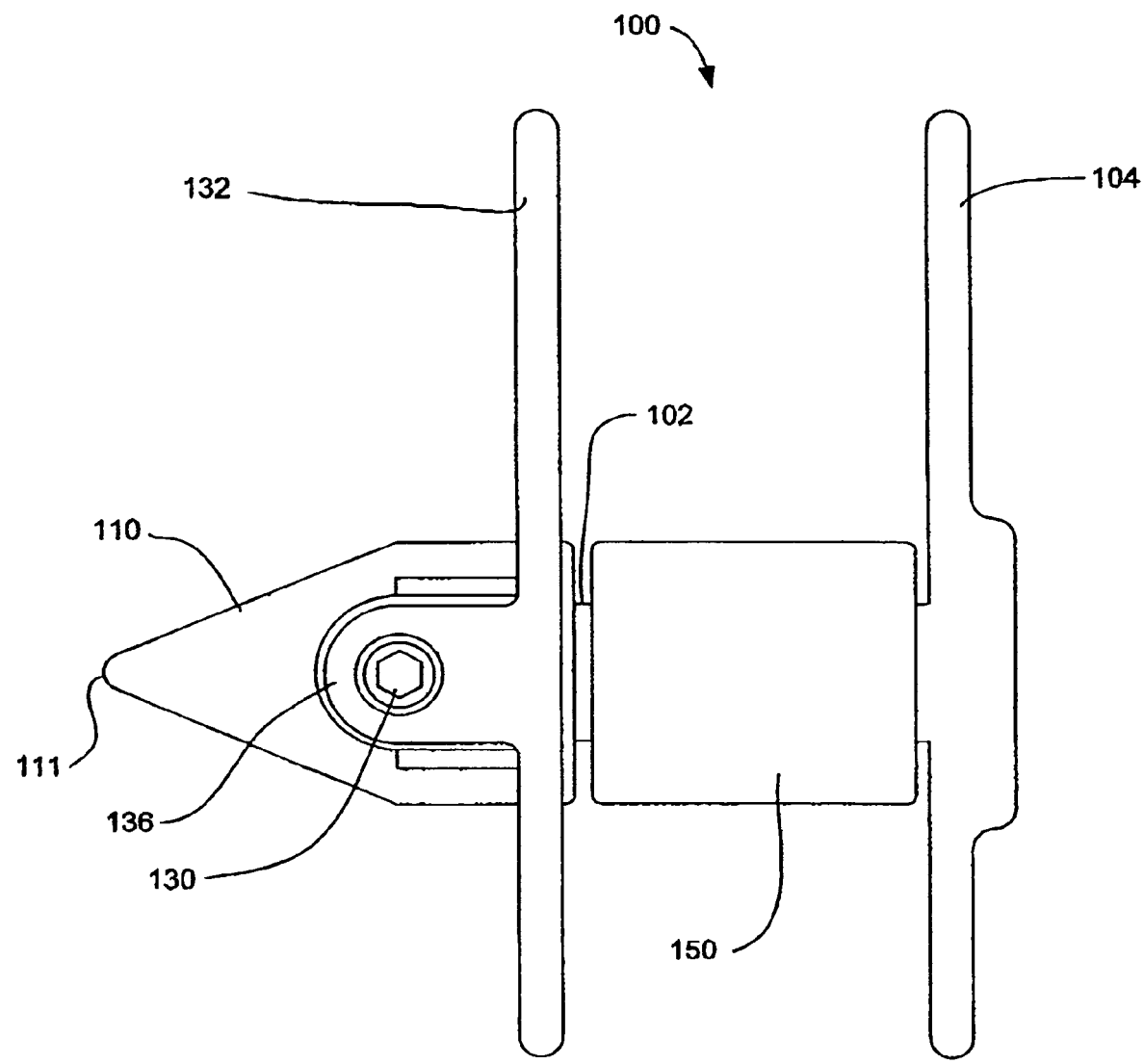

What is disclosed herein is a device that limits spinal extension without limiting spinal flexion. More specifically, the embodiments of the device disclosed herein act to limit extension (backward bending) of the spine without inhibiting the flexion (forward bending) of the spinal column.

The disclosed device is made in part or entirely from bioresorbable materials. The device is used to distract the spinous processes of adjacent vertebrae in order to increase the volume of the spinal canal, and concomitantly relieve intervertebral load. In this regard, the bioresorbable device may be used in procedures where temporary increase in spinal canal volume and relief of intervertebral load is indicated for remediation of an adverse spinal cord condition. Such distraction as a part of surgical remediation of spinal disorders may be performed either before or after the remediation procedure is performed. Remediation includes replacement or repair, or both of an affected part or parts of the spine. For example, remediation of the intervertebral disk may include either disk replacement or disk repair, as well as repair of one part of the disk; the annulus for example, and replacement of another; the nucleus for example. One feature of a bioresorbable device is that it does not require an additional surgery for removal after temporary use.

A bioresorbable material is a material that is broken down by natural processes, and removed thereby. Classes of materials that are useful as bioresorbable materials include polymers, ceramics, and glasses. Polymers of interest include polyesters, polyether esters, polycarbonates, polysaccharides, polyanhydrides, polyurethanes, and polyamide, including copolymers, composites, and blends thereof, as well as composites and blends with ceramics, glasses, and graphite, and the like. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer, the constituents of which are in principle separable by physical means. Fillers, which are solid extenders, may be added to a polymer, copolymer, polymer blend, or polymer composite. Fillers are added to modify properties, such as mechanical, optical, and thermal properties. For bioresorbable materials, it may be desirable to add a filler that would reinforce the material mechanically to enhance strength for certain uses, such as load bearing devices. Bioresorbable ceramics, glasses, and graphite are examples of classes of materials that are desirable for use as fillers to enhance polymer material strength. It may be desirable to add reinforcement elements to a bioresorbable polymer matrix that have the same chemical composition as the polymer matrix. In this instance, the material is referred to as self-reinforced ("SR").

Polyesters are a diverse class of polymers with a number of bioresorbable materials of interest. Poly ether esters are a closely related group, and due to the ester functionality, share many of the same properties of members of the polyester class. Since esters are a condensation polymer, they are easily degraded by hydrolytic processes. Moreover, the materials of interest are also biocompatible materials, meaning that they cause no untoward effect to the host; e.g., excessive inflammation, thrombosis, and the like. Additionally, these bioresorbable polyesters are readily broken down in vivo and eventually excreted in a biocompatible fashion.

Polyesters meeting the criteria of biocompatible, bioresorbable materials include polymers made from monomers of hydroxy acids such as the α-hydroxylactic acid, α-hydroxyglycolidic acid, β-hydroxybutyric acid, γ-hydroxycaprolic acid, and δ-hydroxvaleric acid. Fumaric acid and hydroxyalkanes, such as propylene glycol, butylene glycol, etc., form copolymers that are also candidate bioresorbable polyesters. An example of a biodegradable poly ether ester is poly(dioxanone).

Frequently, the starting materials are condensation products of the free acids, producing cyclized structures used as the monomer starting materials. Poly(dioxanone) is formed from the cyclized monomer, p-dioxanone. For the lower molecular weight hydroxyl acids, two molecules of hydroxy acid may be condensed to form a cyclized monomer. In the case of lactic acid, the corresponding cyclized condensation product of two lactic acid molecules is referred to commonly as a lactide. In the case of glycolic acid, the resultant molecule is referred to commonly as a glycolide. In this regard, whether one starts with lactic acid, or forms thereof, or with lactide, the resultant polymer is a homopolymer of lactic acid. Similarly, in the case of glycolic acid, or forms thereof, and glycolide, regardless of the starting monomer, the resultant polymer is a homopolymer of glycolidic acid. The higher molecular weight hydroxyl acids can undergo an internal cyclization to form lactones that may be used as starting monomers, as can the uncyclized monomer forms. Examples of these include caproic acid, which forms ε-caprolactone, and valeric acid, which forms δ-valerolactone. Again, whether the cyclized monomer, or the free acid monomer, or forms thereof are used as starting materials, homopolymers of the corresponding acids will result. In terms of the common nomenclature for designating these polymers, either form of the starting material may be used to refer to the polymer formed thereby. Hence, reference to polylactide is equivalent to polylactate, since both are homopolymers of lactic acid.

Stereoisomers of the lactic acid, and lactide exist. The properties of the copolymers formed from the stereoisomers of lactide may vary considerably. Interestingly, there is no linear relationship between properties of homopolymers, and their corresponding copolymers. In that regard, a 70:30 copolymer of poly-L-lactide with poly-D,L-lactide produces a material that has a degradation time of thirty-six months, while the degradation time of poly-D,L-lactide is about twelve months and that of poly-L-lactide is greater than twenty-four months. As another example, a 50:50 copolymer blend of glycolide with D,L lactide produces a material that degrades in about two months, while the degradation of poly-D,L-lactide and polyglycolide is about twelve months.

Major suppliers of bulk biodegradable polyester materials include Boehringer Ingelheim, Purac, and Dow. Boehringer Ingelheim's extensive RESOMER® line includes a variety of medical grade poly(L-lactide), poly(D,L-lactide), poly(L-lactide-co-D,L-lactide), poly(L-lactide-co-glycolide), poly(L-lactide-co-ε-caprolactone), poly(L-lactide-co-trimethylene carbonate), and poly(dioxanone) resins for fabrication of the disclosed device. Similarly, Purac's PURASORB® line includes lactide and glycolide monomers, as well as polylactide, polyglycolide, and polylactide/glycolide copolymer resins. Dow's Tone™ products include high molecular weight polycaprolactone resins of high crystallinity. Metabolix Inc. is a supplier of a family of poly(hydroxybutryate-co-valerate) copolymer resins under the trade name Biopol.

Polycarbonates have strength properties desirable for biocompatible, bioresorbable load bearing implants. The copolymerization of lactide or glycolide with trimethylene carbonate produces poly(lactide-co-trimethylene carbonate) and poly(glycolide-co-trimethylene carbonate), respectively. These copolymers have been used to make a range of products from sutures to tacks and screws. Tyrosine derived polycarbonates such as poly(desaminotyrosyl-tyrosine ethyl carbonate) and poly(desaminotyrosyl-tyrosine hexyl carbonate) have also been used in orthopedic applications, such as bone pins and screws. As mentioned above, Boehringer Ingelheim is a bulk supplier of a poly(L-lactide-co-trimethylene carbonate) resin, RESOMER® LT 706. Additionally, Integra Life Sciences is a supplier of tyrosine polycarbonates.

Other examples of biocompatible, bioresorbable classes of polymers are polysaccharides and polyanhydrides. Polysaccharides are a diverse class and include glucans and glycosaminoglycans. Glucans are any homopolymer of glucose, and include celluloses, starches, and dextroses. Starch blends have properties desirable for load-bearing biocompatible, bioresorbable implants. Blends exhibiting good strength characteristics include starch/cellulose acetate blends, starch/polycaprolactone blends, as well as starch blended with copolymers of ethylene and vinyl alcohol. Glucosaminoglycans includes hyaluronates, dermatan sulfates, chondroitin sulfates, heparins, keratans, chitins, and chitosans. The glucosaminoglycans are a ubiquitous class polysaccharides occurring naturally as structural materials, and show potential for as polymers and copolymers for biocompatible, bioresorbable implants. Polyanhydrides are formed by the condensation of diacid molecules. One example of a bioresorbable polyanhydride copolymer is the condensation of sebacic acid ("SA") with hexanedecandioic acid ("HAD") to form poly ("SA-co-HAD") anhydride.

It should be noted that there are two important phases of the process of bioresorption: time to complete loss of strength of the material, and time to complete resorption. There are several factors that affect the rate of degradation of bioresorbable materials, and hence both the time to complete loss of strength, and time to complete resorption. In general, reduction in strength follows the reduction in molecular weight of a polymeric material as it degrades. Factors that affect degradation of bioresorbable polymers include the crystalline nature of the starting material, the hydrophilic nature of the polymer backbone, whether or not the polymer has a reinforcing filler, the initial molecular weight of the polymer, the degree of porosity of the polymer material, the surface area to mass ratio of the device, and the degree of stress on the implanted device.

An example of how the crystalline versus amorphous nature of the starting material impact degradation is illustrated in comparing the properties of poly-L-lactide versus poly-D,L-lactide. The time to complete loss of strength of poly-D,L-lactide is about 6 months, while that of poly-L-lactide is more than 12 months. Recalling from the above, poly-D,L-lactide degrades more rapidly (12 months) than poly-L-lactide (24 months). The racemic mixture of the stereoisomer produces significantly amorphous powders, which yield lower strength materials degrading more rapidly than polymers made from their highly crystalline counterpart. Still another example of how the crystalline versus amorphous nature of a material affects degradation time comes from the previously given example of a 50:50 copolymer blend of glycolide with D,L lactide. This copolymer exhibits a highly amorphous state, and produces a material that degrades significantly faster (two months) than the degradation of poly-D,L-lactide and polyglycolide (twelve months).

Concerning the hydrophilic nature of the polymer backbone, an example of how this property impacts degradation is demonstrated through the comparison of the stability of poly-L-lactide against polyglycolide. Poly-L-lactide has an increased hydrophobic nature (decreased hydrophilic nature) compared with polyglycolide, due to the methyl group in the backbone structure, and is therefore less susceptible to hydrolysis. The time to complete loss of strength of poly-L-lactide is greater than twelve months, while that of polyglycolide is about two months. The comparative degradation times for poly-L-lactide and polyglycolide are twenty-four months versus about six to twelve months, respectively.

The impact of reinforcing filler on increasing material strength can be understood by comparing poly-L-lactide to SR poly-L-lactide properties. Time to complete loss of strength for poly-L-lactide is greater than twelve months, while for SR poly-L-lactide is about eighteen months, while the degradation times are about twenty-four months and seventy-two months, respectively. Other types of reinforcing fillers include ceramics, glasses, and graphite fibers. Ceramics including hydroxyapaptite and tricalcium phosphate, and blends thereof are commonly used reinforcing bioresorbable materials. Bioglasses are silicate glasses containing sodium, calcium, and phosphate as the main components. Ceramics, bioglasses, and bioglass/ceramic compositions have been used in numerous polymer and copolymer bioresorbable material blends to add strength to these materials. The bioresorption of the inorganic ceramic and glass materials follows as the dissolution of the ions, and bioresorption thereof.

In addition to the molecular properties influencing material properties that impact degradation, bulk properties of the material, such as the porosity of material, as well as properties of the device, such as the surface area to mass ratio, affect degradation time, as well. As previously mentioned, there are two phases to the degradation process: time to complete loss of strength and time to complete resorption. These two phases of degradation correlate to two distinct processes: (1) water penetration into the material, with initial degradation of polymer chains, referred to as the hydrolysis phase; and (2) degradation of material strength and fragmentation, and procession of enzymatic attack, phagocytosis, and metabolism. This phase is referred to as metabolism or bulk erosion. Increased porosity of a device and increased relative surface area to mass of a device will enhance the hydrolysis phase, and hence tend to hasten the overall degradation process.

Regarding the impact of degradative processes on the site of the implant, as loss of strength proceeds, the implant will begin to fragment. Increased stress on the implant, and increased vascularization may increase the degradation time. Stress may have a role in decreasing structural integrity, and the increase in the rate of water absorption thereby, and hence affect the rate of bulk erosion. Once the polymer has fragmented into small pieces, in vivo processes, such as phagocytosis, and enzymatic activity speeding up the hydrolysis process may proceed to hasten in the bioresorption process. Such in vivo processes are enhanced by increased vascularization. The presence of the small particles, as well as a local drop in tissue pH in the case of ester hydrolysis due to increased levels of free acid, induces an inflammatory response in the tissue. When bioresorption is complete, the inflammatory response subsides. In that regard, it may be desirable, depending on the use of the device, to fabricate devices from polymers that take longer to complete loss of strength, and have slower rates of degradation.

By what is disclosed of molecular properties, bulk material properties, device design, and factors at the site of implantation, it is therefore possible to design devices from selected materials accordingly.

The following description is presented to enable any person skilled in the art to make and use the disclosed device. Various modifications to the embodiments described will be readily apparent to those skilled in the art, and the principles defined herein can be applied to other embodiments and applications without departing from the spirit and scope of the present disclosure as defined by the appended claims. Thus, the present disclosure is not intended to be limited to the embodiments shown, but is to be accorded the widest scope consistent with the principles and features disclosed herein.

An embodiment of an implant 100 of the disclosed device is depicted in FIG. 1A. This implant 100 includes a first wing 104 and a spacer 150 and a lead-in tissue expander or distraction guide 110. This embodiment further can include, as required, a second wing 132. As can be seen in FIG. 1A, a central body 102 extends from the first wing 104 and is the body that connects the first wing 104 to the tissue expander or distraction guide 110. Also, as can be seen in FIG. 1A and 1B, the distraction guide 110 in this particular embodiment acts to distract the soft tissue and the spinous processes when the implant 100 is inserted between adjacent spinous processes. In this particular embodiment, the distraction guide 110 has an expanding cross-section from the distal end 111 to the area where the second wing 132 is secured to the distraction guide 110. In this embodiment the distraction guide 110 is wedge-shaped.

Figure 1F:
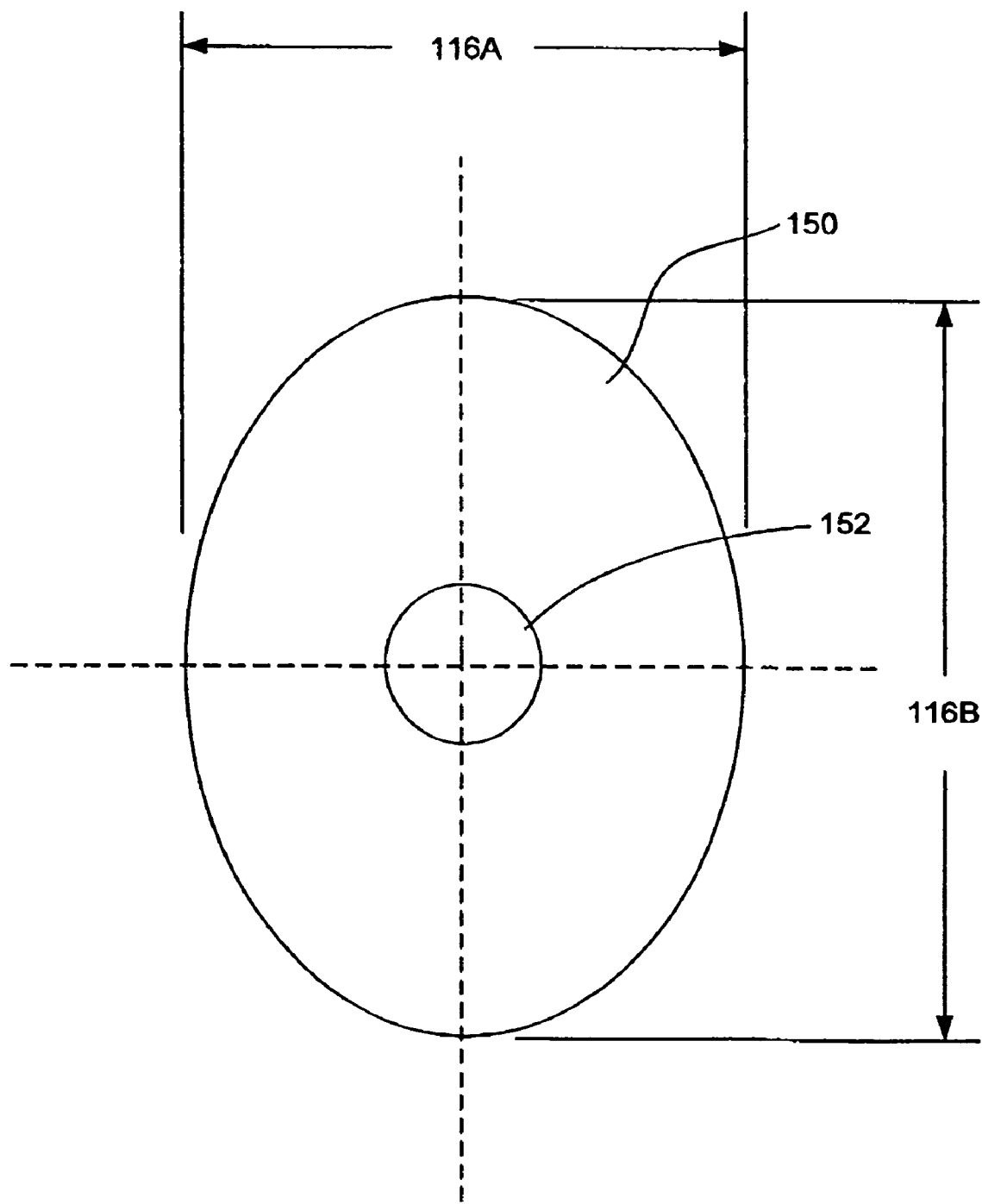

Additionally, as can be seen in FIG. 1A, and 1F, the spacer 150 is elliptical shaped in cross-section. The spacer 150 can have other shapes such as circular, oval, ovoid, football-shaped, and rectangular-shaped with rounded corners and other shapes, and be within the spirit and scope of what is disclosed. In this embodiment, spacer 150 includes a bore 152 which extends the length of spacer 150. The spacer 150 is received over the central body 102 of the implant 100 and can rotate thereon about the central body 102. In these embodiments, the spacer 150 can have minor and major dimensions as follows:

| MINOR DIMENSION (116A) | MAJOR DIMENSION (116 B) |
| --- | --- |
| 6 mm | 13.7 mm |
| 8 mm | 14.2 mm |
| 10 mm | 15.2 mm |
| 12 mm | 16.3 mm |
| 14 mm | 17.8 mm |

The advantage of the use of the spacer 150 as depicted in the embodiment of FIG. 1A is that the spacer 150 can be rotated and repositioned with respect to the first wing 104, in order to more optimally position the implant 100 between spinous processes. It is to be understood that the cortical bone or the outer bone of the spinous processes is stronger at an anterior position adjacent to the vertebral bodies of the vertebra than at a posterior position distally located from the vertebral bodies. Also, biomechanically for load bearing, it is advantageous for the spacer 150 to be close to the vertebral bodies. In order to facilitate this and to accommodate the anatomical form of the bone structures, as the implant is inserted between the spinous processes and/or urged toward the vertebral bodies, the spacer 150 rotates relative to the wings, such as wing 104, so that the spacer 150 is optimally positioned between the spinous processes, and the wing 104 is optimally positioned relative to the spinous processes. Further, the broad upper and lower surfaces of the spacer 150 helps spread the load that the spinous processes place on the spacer 150.

As may be required for positioning the implant 100 between the spinous processes, implant 100 can also include a second wing 132 (FIG. 1E) which fits over the distraction guide 110 and is secured by a bolt 130 (FIG. 1A) placed through aperture 134 provided in a tongue 136 of second wing 132 (FIG. 1E). The bolt 130 is received and secured in the threaded bore 112 located in distraction guide 110. As implanted, the first wing 104 is located adjacent to first sides of the spinous processes and the second wing 132 is located adjacent to second sides of the same spinous processes.

In another embodiment, the spacer 150 has a cross-section with a major dimension and a minor dimension, wherein the major dimension is greater than the minor dimension and, for example, less than about two times the minor dimension.

Figure 2:
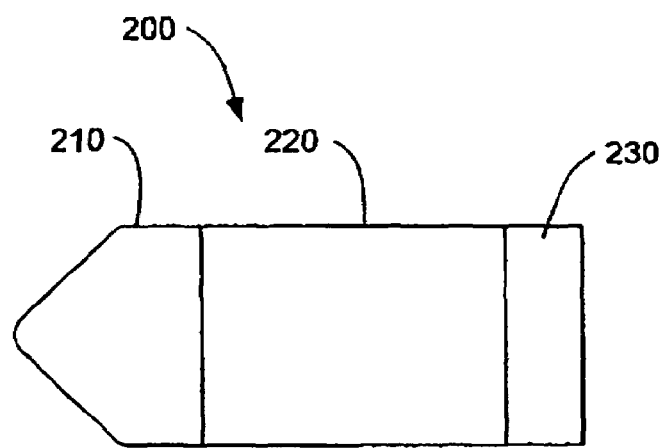
FIG. 2 is a front plan view of a second embodiment of the disclosed device, including an end piece, a spacer, and a distraction guide.

Implant 200 is depicted in FIG. 2. This implant is similar to the implants 100 of FIG. 1, except that this implant does not have either first or second wings. Implant 200 includes a distraction guide 210, spacer 220 which surrounds a central body just as central body 102 of implant 100 in FIG. 1, and endpiece 230. The distraction guide 210 in this preferred embodiment is cone-shaped, and is located at one end of the central body (not shown). At the other end is an endpiece 230. Endpiece 230 is used to contain the other end of the spacer 220 relative to the central body. This embodiment is held together with a bolt (not shown).

Figure 3:
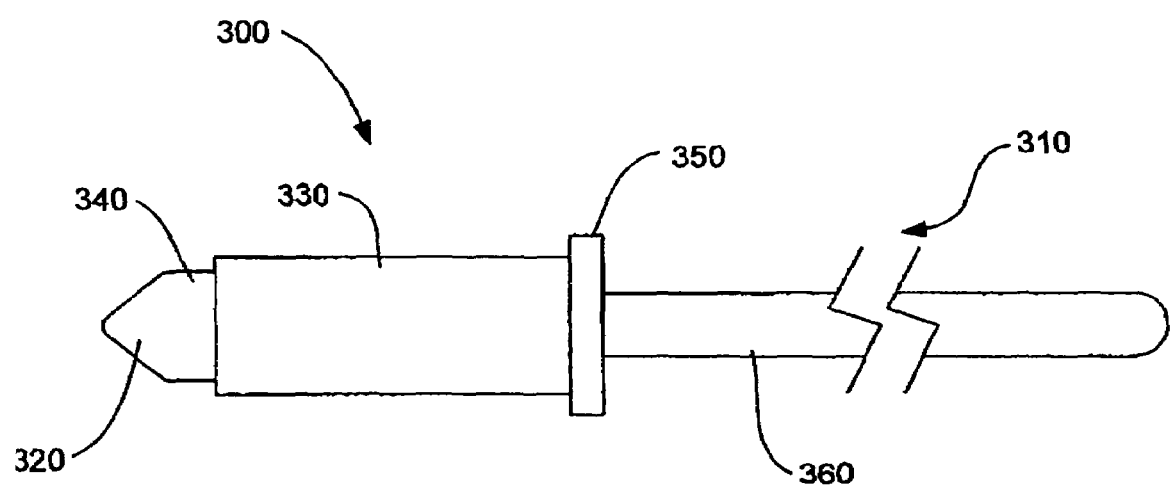
FIG. 3 is a front plan view of a third embodiment of the disclosed device, which is an implant system including an insertion tool comprised of a distraction guide, a central body, a stop and a handle, with a spacer around the central body.

FIG. 3 depicts an implant system 300. Implant system 300 includes an insertion tool 310. Insertion tool 310 includes a distraction guide 320 which in a preferred embodiment is substantially cone-shaped. Distraction guide 320 guides the insertion of the spacer 330 and the insertion tool 360 between adjacent spinous processes. The insertion tool 310 further includes a central body 340, a stop 350, and a handle 360. The distraction guide 320 at its base has dimensions which are slightly less than the internal dimensions of the spacer 330 so that the spacer can fit over the distraction guide 320 and rest against the stop 350. The tool 310 with the distraction guide 320 is used to separate tissues and ligaments and to urge the spacer 330 in the space between the spinous processes. Once positioned, the distraction guide insertion tool 310 can be removed leaving the spacer 330 in place.

For the implants 200 of FIG. 2 and 300 of FIG. 3, such devices would be appropriate where the anatomy between the spinous processes was such that it would be undesirable to use either a first or second wing. However, these embodiment afford all the advantageous described hereinabove (FIGS. 1A-1F) with respect to the distraction guide and also with respect to the dynamics of the spacer.

Additionally, for the embodiments shown in FIGS. 2 and 3, the device may be secured in place via bioresorbable sutures or screws. The degradation times of sutures made from bioresorbable polymers are influenced by both the suture size and type of polymer. Suture products such as Maxon (Davis and Geck), a polyglyconate based suture material, and PDS (Ethicon), a polydioxanone based suture material, maintain tensile strength for four to six weeks, and may take up to six months to be resorbed completely. Depending on the material used, as detailed above, screws may have total time to resorption from six months to five years. Biologically Quite (Instrument Makar), a poly(D,L-lactide-co-glycolide) screw degrades in about six months, while Phusiline (Phusis), a poly(L-lactide-co-D,L lactide) copolymer degrades in about five years, and Bioscrew (Linvatec), a ploy(L-lactide) screw degrades in the range of two to three years.

Figure 4A:
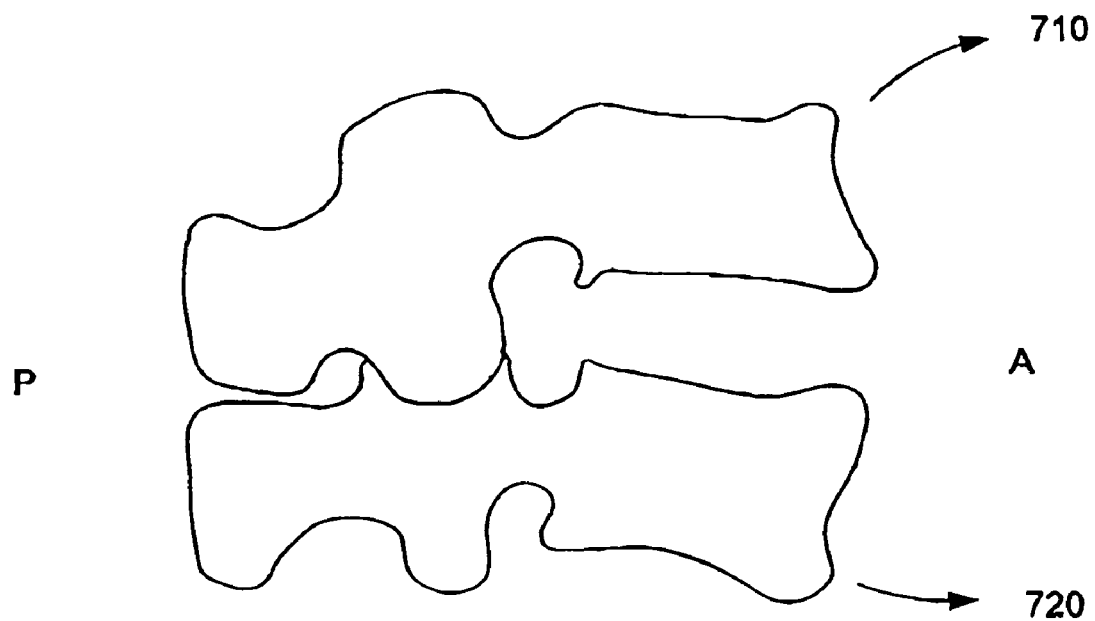
FIGS. 4A and 4B depict the use of the embodiment of FIG. 1A for distraction between vertebrae.
Figure 4B:
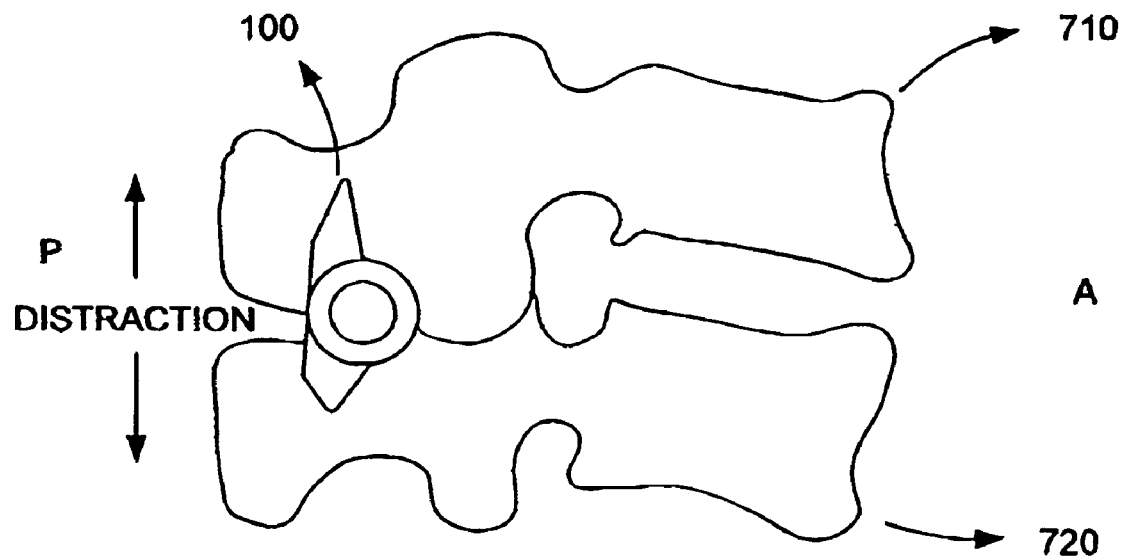

In FIGS. 4A, 4B, what is shown is the view of the device 100 inserted between the spinous processes, so as to distract the two vertebrae 410, 420, thereby increasing the volume of the spinal canal, and concomitantly relieving the intervertebral load. The anterior direction is denoted "A," and the posterior direction is denoted "P."

The implants described also can be used with other elements that further stabilize the spine and the implant's 100 location in the spine as it functions to increase temporarily the volume of the spinal canal and to relieve the intervertebral load. For example, the implants 100, 200, and 300 can be used with a tether or suture which is fitted and secured around adjacent spinous processes. The tether or suture (these terms to be used interchangeably herein) can be made of biocompatible, bioresorbable material(s) described above and as such, the tether need not be explanted, sparing the patient from additional surgery.

Figure 5:
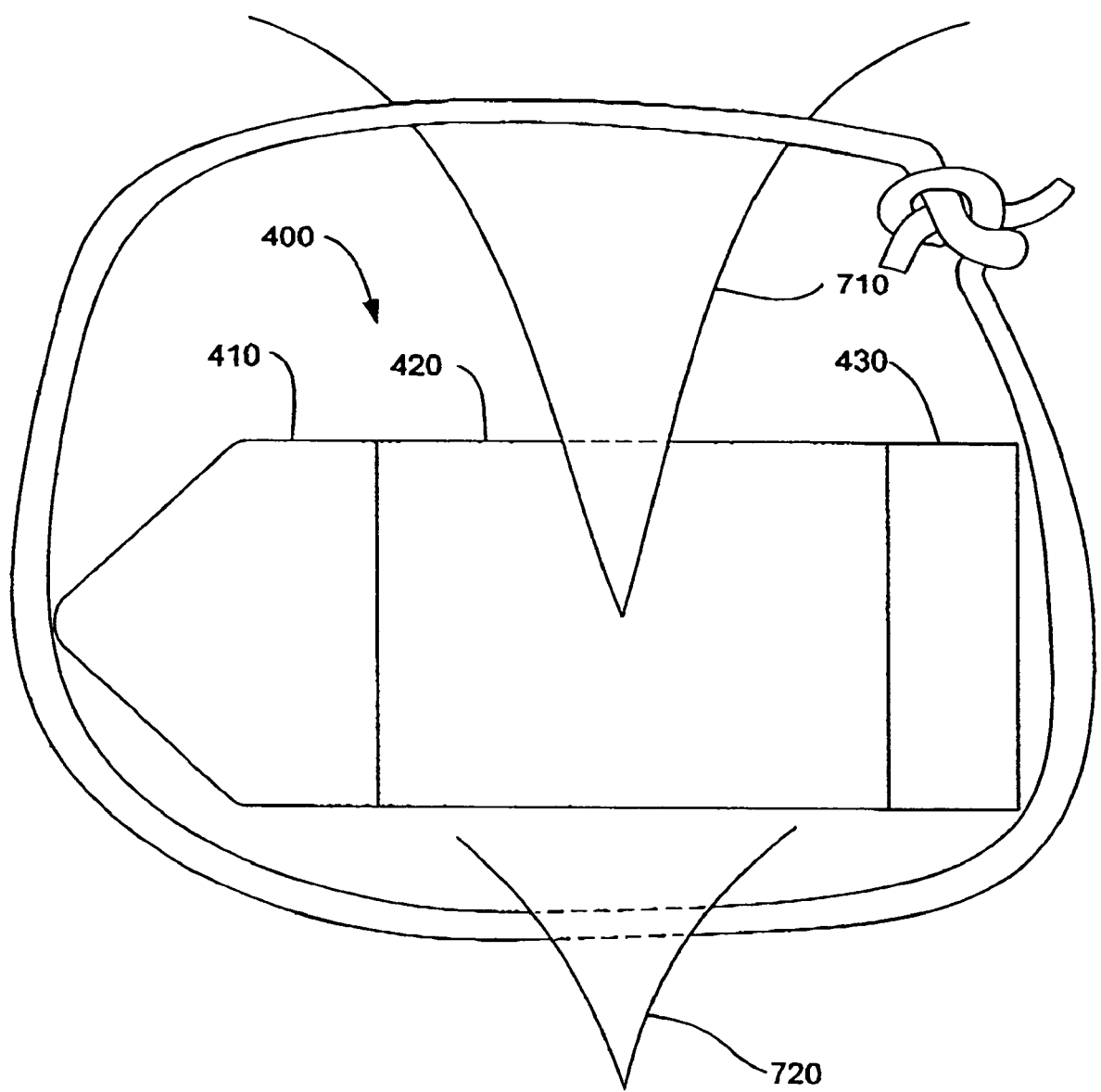
FIG. 5 depicts a further embodiment of the apparatus of the invention based on the embodiment in FIG. 2.

A first use of a tether is depicted in FIG. 5. In this embodiment 400, an implant such as implant 100 or 200 can be positioned between a upper spinous process 710 and a lower spinous process 720, and a tether 470 can loop around the upper spinous process 710 and the lower spinous process 720. The tether 470 need not interact with the implant 100, 200, or 300; that is, there need not be a fastening mechanism to connect the implant 100, 200, or 300 with the tether 470. Instead, the ends of tether 470 can be fastened together in a loop by any suitable mechanism. Alternatively, the ends can be knotted or stitched to fasten them through the bores.

Figure 6:
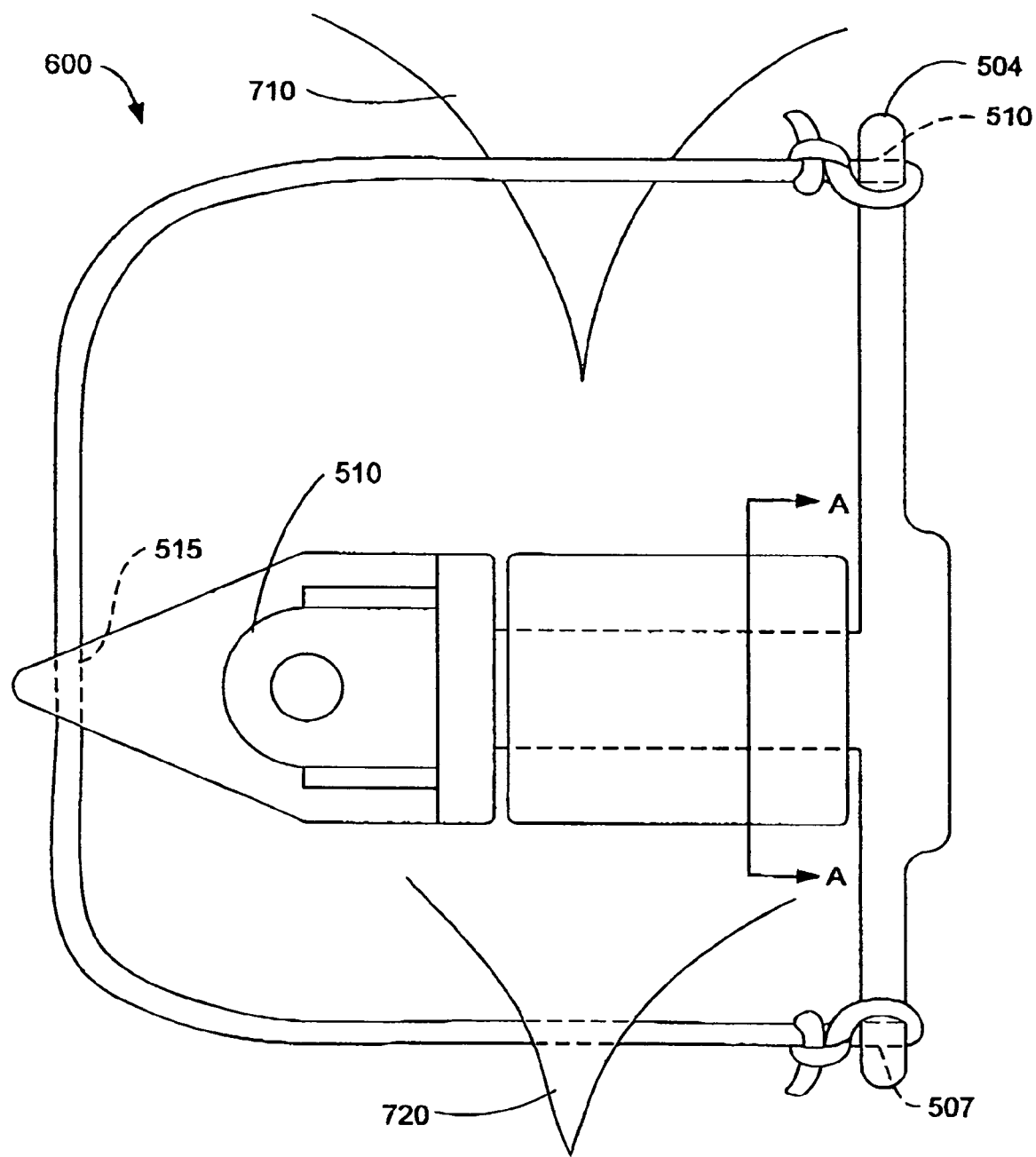
FIG. 6 depicts a further embodiment of the apparatus of the invention based on the embodiment in FIG. 1C.

A further use of the tether is depicted in FIG. 6. In this embodiment 500, based upon implant 100, the tether 570 fastens to an upper bore 505 of the first wing 504, and loops around the upper spinous process 710 to be threaded through a bore 515 through the distraction guide 510. The tether 570 then continues to loop around by passing around the lower spinous process 720 and fastens to a lower bore 507 in the first wing 504. The tether 570 can be fastened at the upper bore 505 and lower bore 507 of the first wing 504 by an appropriate fastening means, such as a cuff made of biocompatible, bioresorbable material. Alternatively, the ends of the tether 570 fastened to the upper bore 505 and lower bore 507 can be knotted or tied off, or sewn with sutures.

Figure 7:
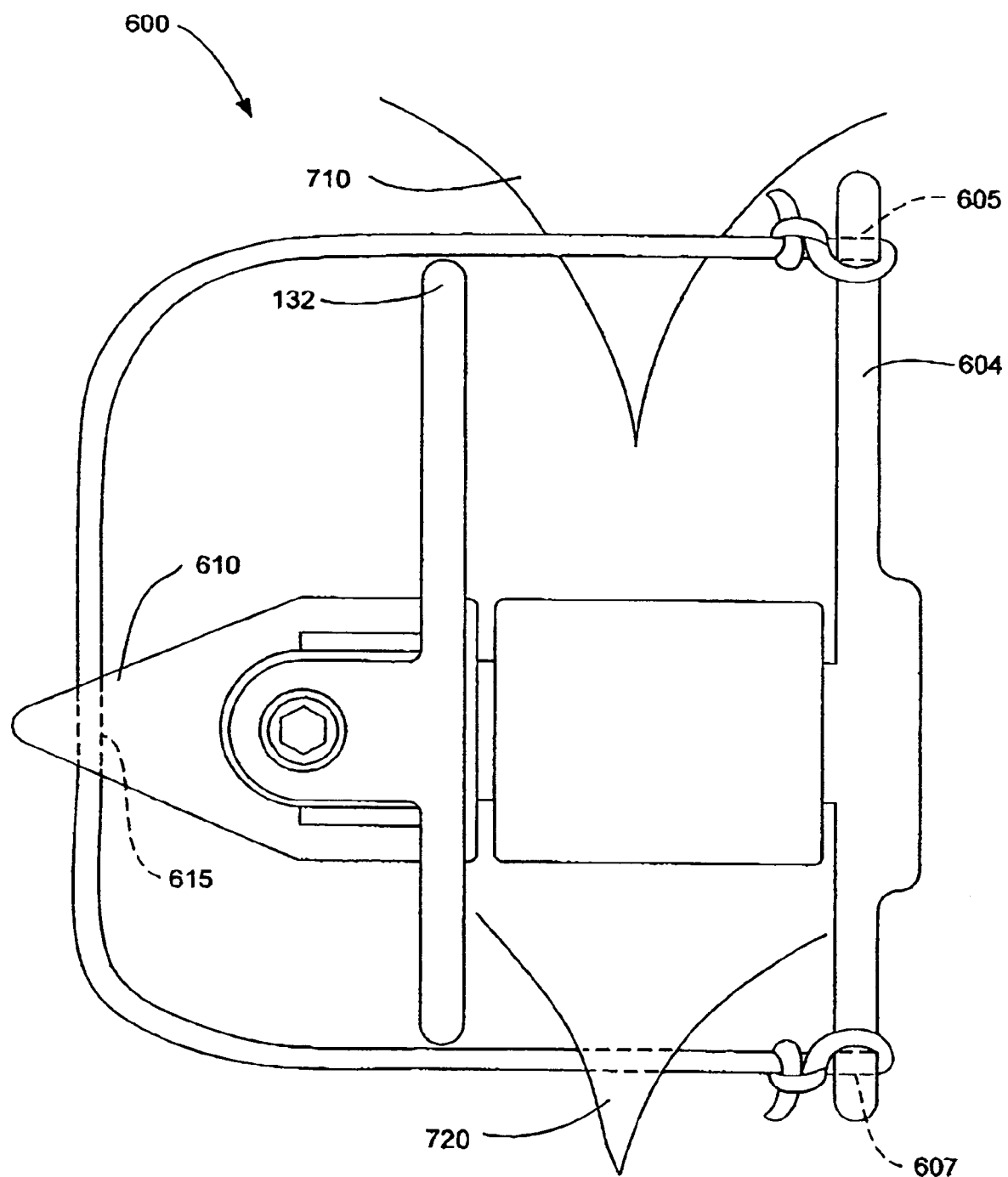
FIG. 7 depicts a further embodiment of the apparatus of the invention based on the embodiment in FIG. 1A.

As depicted in FIG. 7, a tether also can be used in conjunction with implant 100 where implant 100 has a second wing 632. The tether 670 need not pass through or connect with the second wing 632. Instead, the tether 670 fastens with an upper bore 605 in a first wing 604 and passes around an upper spinous process 710 and can then pass through a bore 615 in the distraction guide 610. The tether 670 then passes under the lower spinous process 720 and fastens with a lower bore 607 through the first wing 604. The tether 670 can be fastened at the upper bore 605 and lower bore 607 of the first wing 604 by an appropriate fastening means, such as a cuff made of biocompatible, bioresorbable material. Alternatively, the ends of the tether 670 fastened to the upper bore 605 and lower bore 607 can be knotted or tied off, or sewn with sutures.

One use contemplated for such devices is implantation in conjunction with intervertebral disk remediation, either implanting a disk replacement device or performing surgical repair on an intervertebral disk. Devices and methods suitable for disk replacement have been described in U.S. patent application Ser. No. 10/685,134, filed Oct. 14, 2003, entitled "TOOLS FOR IMPLANTING ARTIFICIAL VERTEBRAL DISK AND METHOD," U.S. patent application Ser. No. 10/684,669, filed Oct. 14, 2003, entitled "ARTIFICIAL VERTEBRAL DISK REPLACEMENT IMPLANT WITH TRANSLATING PIVOT POINT AND METHOD," U.S. Provisional Patent Application No. 60/526,724, filed Dec. 2, 2003, entitled "ARTIFICIAL VERTEBRAL DISK REPLACEMENT IMPLANT WITH TRANSLATING PIVOT POINT AND LATERAL IMPLANT METHOD," U.S. patent application Ser. No. 10/981,863, filed Nov. 5, 2004, entitled "LATERALLY INSERTABLE ARTIFICIAL DISK REPLACEMENT IMPLANT WITH TRANSLATING PIVOT POINT," U.S. patent application Ser. No. 10/981,807, filed Nov. 5, 2004, entitled "METHOD OF LATERALLY INSERTING AN ARTIFICIAL VERTEBRAL DISK REPLACEMENT IMPLANT WITH TRANSLATING PIVOT POINT," U.S. patent application No. 10/684,668, filed Oct. 14, 2003, entitled "ARTIFICIAL VERTEBRAL DISK REPLACEMENT IMPLANT WITH CROSSBAR SPACER AND METHOD," U.S. Provisional Application No. 60/517,973, filed Nov. 6, 2003, entitled "ARTIFICIAL VERTEBRAL DISK REPLACEMENT IMPLANT WITH CROSSBAR SPACER AND LATERAL IMPLANT METHOD," U.S. patent application No. 10/685,011, filed Oct. 14, 2003, entitled "ARTIFICIAL VERTEBRAL DISK REPLACEMENT IMPLANT WITH A SPACER AND METHOD," and U.S. Provisional Application No. 60/524,350, filed Nov. 21, 2003, entitled "ARTIFICIAL VERTEBRAL DISK REPLACEMENT IMPLANT WITH A SPACER AND LATERAL IMPLANT METHOD," U.S. patent application No. 10/981,923, filed Nov. 5, 2004, entitled "LATERALLY INSERTABLE ARTIFICIAL VERTEBRAL DISK REPLACEMENT IMPLANT WITH CURVED SPACER," U.S. patent application No. 10/981,945, filed Nov. 5, 2004, entitled: "METHOD OF LATERALLY INSERTING AN ARTIFICIAL VERTEBRAL DISK REPLACEMENT IMPLANT WITH CURVED SPACER," and are incorporated herein by reference. In addition to the total disk replacement devices described in the aforementioned applications, polymer-filled implants based on a biomimetic approach to disk repair and replacement may be used for remediation. Devices and methods describing the use of such implants are found in U.S. Pat. No. 6,416,766, issued Jul. 9, 2002, entitled "BIOLOGICAL DISK REPLACE- MENT BONE MORPHOGENIC PROTEIN (BMP) CARRIERS AND ANTI-ADHESION MATERIALS," and U.S. patent application Ser. No. 09/815,387, filed Mar. 22, 2001, entitled "IMPLANTABLE PROSTHETIC OR TISSUE EXPANDING DEVICE," both incorporated herein by reference.

FIG. 8 is a flowchart showing an embodiment of the method of the present invention. Regarding the disclosed devices used in conjunction with disk remediation implants and procedures like those described by the aforementioned incorporated references, load relief of the vertebral disks, either before or after a disk remediation procedure is done 820, is indicated either to assist in the process of disk remediation, or to allow for effective recovery of the surgical procedure, or both. Moreover, the disclosed devices, made in part or completely from the biocompatible, bioresorbable materials described in this disclosure, require no additional surgical procedure for removal after recovery is complete.

The bioresorbable load relief/spinal distraction devices disclosed above can be inserted laterally. The implanting physician after accessing the intervertebral space 810 optionally can distract the spinous process before inserting the device 830, 840. Alternatively, the tissue expander can be used to distract the spinous processes while inserting the device 830, 840.

The spinous processes can be further stabilized by the use of a bioresorbable tether together with the resorbable distracting device adapted to accept the tether 855, or with a bioresorbable device which does not have wings and need not be adapted to accept the tether 850. If the device does not have a first or second wing, the tether is looped around the spinous processes and fastened, after the implant is positioned between the spinous processes 850.

Certain of the bioresorbable devices are adapted to accept the tether so that the tether binds not only the spinous processes but also the implant, to maintain temporarily a minimum spacing between the spinous processes 855. The adaptations include an upper bore and a lower bore on the first wing, and a bore through the distraction guide. During the implantation, the device is inserted between the spinous processes with one first of the tether attached to the upper bore of the first wing. A curved needle or other tool can then be used to lead the second end of the tether over an upper spinous process, through the bore in the tissue expander, under a lower spinous process, and through the lower bore of the first wing, to fasten the second end to the lower bore of the first wing. The tether is tightened to the desired degree to maintain a minimal distraction of the spinous processes and the ends of the tether are fastened 860.

It is within the scope of the present invention to fasten the first end of the tether to the lower bore of the first wing, and to use a curved needle or other implement to lead the second end of the tether below the lower spinous process, through the bore in the tissue expander, over the upper spinous process, and through the upper bore on the first wing, to fasten the second end of the upper bore of the first wing.

Where the implant has a second wing, the same method is followed as for an implant with one wing, as the second wing need not engage the tether.

The foregoing description of embodiments of the present disclosure has been provided for the purposes of illustration and description. It is not intended to be exhaustive or to limit the disclosure to the precise forms disclosed. Many modifications and variations will be apparent to the practitioner skilled in the art. The embodiments were chosen and described in order to best explain the principles of this disclosure and its practical application, thereby enabling others skilled in the art to understand various embodiments and with various modifications that are suited to the particular use contemplated. It is intended that the scope of this disclosure be defined by the following claims and its equivalence.

What is claimed is:

1. A prosthethic device adapted to insert between first and second adjacent spinous processes, said device comprising:
   a central body including an elongated shape with a first end and a second end, the central body being sized to fit between the first and second spinous processes;
   a first wing attached to the first end of the central body;
   a spacer made of a bioresorbable material, the spacer including a bore that is sized to receive the central body with the spacer extending around the central body, the spacer being rotatable with respect to the central body;
   a second wing attached to the central body and positioned on an opposite lateral side of the spacer from the first wing;
   a tissue expander operatively connected to the second end of the central body, the tissue expander including an expanding cross-sectional shape that increases from a tip at a distal end away from the second wing toward an area where the second wing is attached to the central body.

2. The device of claim 1, wherein the bioresorbable material is selected from polyester, polysaccharide, polyanhydride, and polycarbonate, including copolymers, composites, and blends thereof.

3. The device of claim 2, wherein the polyester polymer is selected from polylactide, polyglycolide, poly-E-caprolactone, poly-β-hydroxybutyrate, poly-δ-valerolactone, poly(dioxanone), and poly(ethylene terephthlate).

4. The device of claim 2, wherein the polysaccharide polymer is a selected from glucans and glucosaminoglycans.

5. The device of claim 2, wherein the polycarbonate polymer is selected from poly(desaminotyrosyl-tyrosine ethyl) carbonate, and poly(desaminotyrosyl-tyrosine hexyl)carbonate.

6. The device of claim 2, wherein the polyester copolymers are selected from poly(L-lactide-co-glycolide), poly(D,L-lactide-co-glycolide), poly(lactide-co-trimethylene carbonate), poly(D,L-lactide), poly(L-lactide-co-D,L-lactide), poly(lactide-co-tetramethylglycolide), poly(lactide-co-ϵ-caprolactone), poly(lactide-co-δ-valerolactone), poly(glycolide-co-trimethylene carbonate), poly(glycolide-co-ϵ-caprolactone), poly(glycolide-co-δ-valerolactone), poly(propylene fumarate), poly(propylene fumarate diacrylate), poly(hydroxybutyrate-co-hydroxyvalerate), and poly(ethylene terephthlate-co-dioxanone).

7. The device of claim 2, wherein the polymer further comprises a filler.

8. The device of claim 7, wherein the filler is selected from at least one of graphite, ceramic, and glass.

9. The device of claim 2, wherein the polymer is self-reinforced.

10. The device of claim 9, wherein the self-reinforced polymer is selected from polyesters and copolymers thereof.

11. The device of claim 1, wherein the central body is constructed of a non-bioresorbable material.

12. The device of claim 11, wherein a diameter of the bore is greater than a width of the central body to allow the spacer to rotate around the central body.

13. The spacer of claim 12, wherein the spacer includes a cross-sectional shape with a major axis and a minor axis such that rotation of the spacer around the central body adjusts an effective height of the spacer.

14. A prosthetic device adapted to insert between first and second adjacent spinous processes, with components comprising:
- a central body with a distal end and a proximal end, said central body having a longitudinal axis;
- a spacer including an aperture sized to receive the central body. the aperture being larger than a width of the central body to allow the spacer to rotate around the central body;
- a tissue expander extending from the distal end of the central body and including a first end positioned away from the spacer and a second end positioned in proximity to the spacer, the tissue expander including a wedge shape with a width that increases along the length from the first end toward the second end; and
- a wing attached to the proximal end of the central body;
- wherein the central body and the spacer are sized to fit between the spinous processes with a first surface of the spacer in contact with the first spinous process and a second surface of the spacer in contact with the second spinous process, and the wing including a greater height than the spacer to extend outward beyond the first and second surfaces and along a lateral side of the first and second spinous processes;
- wherein at least one of the central body, spacer. tissue expander, and wing is made of a bioresorbable material.

15. The device as in claim 14 further comprising a tether made of a bioresorbable material, wherein the tether loops around adjacent spinous processes and the ends of the tether are fastened together.

16. The device of claim 12, further comprising:
- a second wing located at the distal end of the central body, wherein the spacer is between the wing and the second wing.

17. The device of claim 16, wherein each of the central body, spacer, tissue expander, and wing are made of a bioresorbable material.

18. The device of claim 16, wherein the bioresorbable material is selected from polyester, polysaccharide, and polycarbonate, including copolymers, composites, and blends thereof.

19. The device of claim 18, wherein the polyester polymer is selected from polylactide, polyglycolide, poly-ε-caprolactone, poly-β-hydroxybutyrate, poly-δ-valerolactone, poly(dioxanone), and poly(ethylene terephthlate).

20. The device of claim 18, wherein the polysaccharide polymer is a selected from glucans and glucosaminoglycans.

21. The device of claim 18, wherein the polycarbonate polymer is selected from poly(desaminotyrosyl-tyrosine ethyl)carbonate, and poly(desaminotyrosyl-tyrosine hexyl)carbonate.

22. The device of claim 18, wherein the polyester copolymers are selected from poly(L-lactide-co-glycolide), poly(D,L-lactide-co-glycolide), poly(lactide-co-trimethylene carbonate), poly(D,L-lactide), poly(L-lactide-co-D,L-lactide), poly(lactide-co-tetramethylglycolide), poly(lactide-co-ε-caprolactone), poly(lactide-δ-valerolactone), poly(glycolide-co-trimethylene carbonate), poly(glycolide-co-ε-caprolactone), poly(glycolide-co-δ-valerolactone), poly(propylene fumarate), poly(propylene fumarate diacrylate), poly(hydroxybutyrate-co-hydroxyvalerate), and poly(ethylene terephthlate-co-dioxanone).

23. The device of claim 18, wherein the polymer further comprises a filler.

24. The device of claim 23, wherein the filler is selected from at least one of graphite, ceramic, and glass.

25. The device of claim 18, wherein the polymer is self-reinforced.

26. The device of claim 25, wherein the self-reinforced polymer is selected from polyesters and copolymers thereof.

27. A prosthetic device adapted to insert between first and second adjacent spinous processes, with components comprising:
- a central body with a distal end and a proximal end, said central body having a longitudinal axis;
- a spacer positioned over the central body and rotatably attached to the central body, wherein said spacer is adapted to be placed between the spinous processes, the spacer including an elliptical cross-sectional shape;
- a first wing attached to the proximal end of the central body on a first side of the spacer and a second wing attached to the distal end of the central body on a second side of the spacer, each of the wings extending outward from the central body beyond the spacer in superior and inferior directions;
- a tissue expander extending from the distal end of the central body; and
- wherein at least one of the central body, spacer, first wing, and tissue expander is made of a bioresorbable material.

28. The device of claim 27 further comprising a tether made of a bioresorbable material, wherein the tether loops around adjacent spinous processes and the ends of the tether are fastened together.

29. The device of claim 28 wherein the tether fastens to an upper bore on the first wing, passes over an upper spinous process, a bore in the tissue expander, and a lower spinous process, and fastens to a lower bore on the first wing.

30. The device of claim 27 further comprising a tether made of a bioresorbable material, wherein the tether loops around adjacent spinous processes and the ends of the tether are fastened together.

31. The device of claim 30 wherein the tether fastens to an upper bore on the first wing, passes over an upper spinous process, a bore in the tissue expander, and a lower spinous process, and fastens to a lower bore on the first wing.

32. The device of claim 30, wherein the bioresorbable material is selected from polyester, polysaccharide, and polycarbonate, including copolymers, composites, and blends thereof.

33. The device of claim 32, wherein the polyester polymer is selected from polylactide, polyglycolide, poly-ε-caprolactone, poly-β-hydroxybutyrate, poly-δ-valerolactone, poly(dioxanone), and poly(ethylene terephthlate).

34. The device of claim 32, wherein the polysaccharide polymer is a selected from glucans and glucosaminoglycans.

35. The device of claim 32, wherein the polycarbonate polymer is selected from poly(desaminotyrosyl-tyrosine ethyl)carbonate, and poly(desaminotyrosyl-tyrosine hexyl )carbonate.

36. The device of claim 32, wherein the polyester copolymers are selected from poly(L-lactide-co-glycolide), poly(D,L-lactide-co-glycolide), poly(lactide-co-trimethylene carbonate), poly(D,L-lactide), poly(L-lactide-co-D,L-lactide), poly(lactide-co-tetramethylglycolide), poly(lactide-co-ε-caprolactone), poly(lactide-co-δ-valerolactone), poly(glycolide-co-trimethylene carbonate), poly(glycolide-co-ε-caprolactone), poly(glycolide-co-δ-valerolactone), poly(propylene fumarate), poly(propylene fumarate diacrylate), poly(hydroxybutyrate-co-hydroxyvalerate), and poly(ethylene terephthlate-co-dioxanone).

37. The device of claim 32, wherein the polymer further comprises a filler.

38. The device of claim 37, wherein the filler is selected from at least one of graphite, ceramic, and glass.

39. The device of claim 32, wherein the polymer is self-reinforced.

40. The device of claim 39, wherein the self-reinforced polymer is selected from polyesters and copolymers thereof.

41. The device of claim 27, wherein each of the central body, spacer, first wing, and tissue expander are made of a bioresorbable material.

42. A prosthetic device adapted to insert between adjacent spinous processes, with components comprising:
- a central body with a distal end and a proximal end, said central body having a longitudinal axis;
- a spacer rotatably connected to the central body, wherein said spacer is adapted to be placed between the spinous processes;
- a first wing located at the proximal end of the central body and a second wing located at the distal end of the central body, wherein the spacer is between the first wing and the second wing, each of the first and second wings extending outward from the central body in superior and inferior directions, each of the first and second wings including a greater height than the spacer to extend outward from the central body a greater distance than the spacer in the superior and inferior directions;
- a tissue expander extending from the distal end of the central body, the tissue expander including an expanding cross-section with a narrow tip positioned away from the central body and a wide base positioned towards the central body; and
- wherein at least one of the central body, spacer, first wing, second wing, and tissue expander is made of a bioresorbable material.

43. The device of claim 42 further comprising a tether made of a bioresorbable material, wherein the tether loops around adjacent spinous processes and threads through the device.

44. The device of claim 43 wherein the tether fastens to an upper bore on the first wing, passes over an upper spinous process, a bore in the tissue expander, and a lower spinous process, and fastens to a lower bore on the first wing.

45. The device of claim 42 further comprising a tether made of a bioresorbable material, wherein the tether loops around adjacent spinous processes and threads through the device.

46. The device of claim 45 wherein the tether fastens to an upper bore on the first wing, passes over an upper spinous process, a bore in the tissue expander, and a lower spinous process, and fastens to a lower bore on the first wing.

47. The device of claim 42, wherein each of the central body. spacer, first wing, second wing, and tissue expander are made of a bioresorbable material.

48. The device of claim 42, wherein the bioresorbable material is selected from polyester, polysaccharide, and polycarbonate, including copolymers, composites, and blends thereof.

49. The device of claim 48, wherein the polycarbonate polymer is selected from poly(desaminotyrosyl-tyrosine ethyl)carbonate, and poly(desaminotyrosyl-tyrosine hexyl)carbonate.

50. The device of claim 48, wherein the polyester copolymers are selected from poly(L-lactide-co-glycolide), poly(D, L-lactide-co-glycolide), poly(lactide-co-trimethylene carbonate), poly(D,L-lactide), poly(L-lactide-co-D, L-lactide), poly(lactide-co-tetramethylglycolide), poly(lactide-co-$\epsilon$-caprolactone), poly(lactide-co-$\delta$-valerolactone), poly(glycolide-co-trimethylene carbonate), poly(g lycolide-co-$\epsilon$-caprolactone), poly(glycolide-co-$\delta$-valerolactone), poly(propylene fumarate), poly(propylene fumarate diacrylate), poly(hydroxybutyrate-co-hydroxyvalerate), and poly(ethylene terephthlate-co-dioxanone).

51. The device of claim 48, wherein the polymer further comprises a filler.

52. The device of claim 51, wherein the filler is selected from at least one of graphite, ceramic, and glass.

53. The device of claim 48, wherein the polymer is self-reinforced.

54. The device of claim 53, wherein the self-reinforced polymer is selected from polyesters and copolymers thereof.

55. The device of claim 42, wherein the polyester polymer is selected from polylactide, polyglycolide, poly-$\epsilon$-caprolactone, poly-$\beta$-hydroxybutyrate, poly-$\delta$-valerolactone, poly(dioxanone), and poly(ethylene terephthlate).

56. The device of claim 42, wherein the polysaccharide polymer is a selected from glucans and glucosaminoglycans.

* * * * *